United States Patent
Brittain et al.

(10) Patent No.: US 10,548,905 B2
(45) Date of Patent: Feb. 4, 2020

(54) AMORPHOUS ONAPRISTONE COMPOSITIONS AND METHODS OF MAKING THE SAME

(71) Applicant: CONTEXT BIOPHARMA INC., Philadelphia, PA (US)

(72) Inventors: Harry G. Brittain, Milford, NJ (US); Stefan Proniuk, Austin, TX (US)

(73) Assignee: CONTEXT BIOPHARMA INC., Philadelphia, PA (US)

( * ) Notice: Subject to any disclaimer, the term of this patent is extended or adjusted under 35 U.S.C. 154(b) by 0 days.

(21) Appl. No.: 15/378,004

(22) Filed: Dec. 13, 2016

(65) Prior Publication Data

US 2017/0182065 A1    Jun. 29, 2017

Related U.S. Application Data

(60) Provisional application No. 62/267,540, filed on Dec. 15, 2015.

(51) Int. Cl.
*A61K 31/56* (2006.01)
*A61K 9/00* (2006.01)
*A61K 31/575* (2006.01)
*A61K 9/16* (2006.01)
*C07J 41/00* (2006.01)

(52) U.S. Cl.
CPC .......... *A61K 31/575* (2013.01); *A61K 9/1635* (2013.01); *A61K 9/1641* (2013.01); *A61K 9/1682* (2013.01); *C07J 41/0055* (2013.01)

(58) Field of Classification Search
CPC .............................. A61K 31/57; A61K 9/0087
USPC ........................................ 514/177; 424/400
See application file for complete search history.

(56) References Cited

U.S. PATENT DOCUMENTS

| | | | |
|---|---|---|---|
| 4,742,000 | A | 5/1988 | Greene |
| 4,774,236 | A | 9/1988 | Cook et al. |
| 4,780,461 | A | 10/1988 | Neef et al. |
| 4,843,157 | A | 6/1989 | Neef et al. |
| 5,141,961 | A | 8/1992 | Coapman |
| 5,273,971 | A | 12/1993 | Scholz et al. |
| 5,283,190 | A | 2/1994 | Traish et al. |
| 5,446,036 | A | 8/1995 | Scholz et al. |
| 5,693,628 | A | 12/1997 | Schubert et al. |
| 6,093,707 | A | 7/2000 | Cook et al. |
| 6,143,754 | A | 11/2000 | Chwalisz et al. |
| 6,537,584 | B1 | 3/2003 | Zentner et al. |

(Continued)

FOREIGN PATENT DOCUMENTS

| | | |
|---|---|---|
| CN | 1087090 A | 5/1994 |
| DE | 3321826 A1 | 12/1984 |

(Continued)

OTHER PUBLICATIONS

Neef et al. "New steroids with antiprogestational and antiglucocorticoid activities." Steroids, 1984, vol. 44, No. 4, pp. 349-372.*

(Continued)

*Primary Examiner* — Shengjun Wang
(74) *Attorney, Agent, or Firm* — Pepper Hamilton LLP

(57) ABSTRACT

Amorphous forms of onapristone and methods of making such amorphous forms are provided. Amorphous forms can be characterized by their X-ray powder diffraction patterns and other properties.

7 Claims, 15 Drawing Sheets

(56) References Cited

U.S. PATENT DOCUMENTS

| | | | |
|---|---|---|---|
| 6,750,015 | B2 | 6/2004 | Horwitz et al. |
| 6,900,193 | B1 | 5/2005 | Kim et al. |
| 7,678,781 | B2 | 3/2010 | Fiordeliso et al. |
| 8,121,365 | B2 | 2/2012 | Pinard et al. |
| 8,709,463 | B2 | 4/2014 | Looney et al. |
| 9,046,534 | B2 | 6/2015 | Gilles |
| 9,193,757 | B2 | 11/2015 | Proniuk |
| 9,328,346 | B2 | 5/2016 | Lee et al. |
| 9,618,512 | B2 | 4/2017 | Endou et al. |
| 2003/0099641 | A1 | 5/2003 | Smith et al. |
| 2004/0072811 | A1 | 4/2004 | Hoffmann et al. |
| 2004/0121304 | A1 | 6/2004 | Fuhrmann et al. |
| 2006/0063190 | A1 | 3/2006 | Fischer et al. |
| 2006/0111577 | A1 | 5/2006 | Kim et al. |
| 2007/0166372 | A1 | 7/2007 | Huang et al. |
| 2007/0166753 | A1 | 7/2007 | Mass |
| 2007/0167971 | A1 | 7/2007 | Huey et al. |
| 2008/0200440 | A1 | 8/2008 | Fuhrmann et al. |
| 2011/0003753 | A1 | 1/2011 | Waxman et al. |
| 2011/0053900 | A1 | 3/2011 | Podolski et al. |
| 2011/0293511 | A1 | 12/2011 | Johns et al. |
| 2012/0010790 | A1 | 1/2012 | Kanayama et al. |
| 2012/0140790 | A1 | 6/2012 | Ali et al. |
| 2012/0230983 | A1 | 9/2012 | Muller et al. |
| 2013/0018027 | A1 | 1/2013 | Podolski et al. |
| 2013/0029953 | A1 | 1/2013 | Nickisch et al. |
| 2013/0095170 | A1 | 4/2013 | Gilles |
| 2013/0316992 | A1 | 11/2013 | Lange et al. |
| 2013/0338016 | A1 | 12/2013 | McDonough et al. |
| 2014/0271819 | A1* | 9/2014 | Proniuk ............ C07J 41/0083 424/450 |
| 2014/0363425 | A1 | 12/2014 | Graham et al. |
| 2015/0241432 | A1 | 8/2015 | Berois et al. |
| 2015/0241435 | A1 | 8/2015 | Gilles |
| 2015/0285803 | A1 | 10/2015 | Gilles et al. |
| 2016/0166583 | A1 | 6/2016 | Zukiwski et al. |
| 2017/0088579 | A1 | 3/2017 | Tilstam et al. |
| 2017/0182065 | A1 | 6/2017 | Brittain et al. |
| 2017/0266204 | A1 | 9/2017 | Proniuk et al. |

FOREIGN PATENT DOCUMENTS

| | | |
|---|---|---|
| EP | 0129499 A2 | 12/1984 |
| EP | 0277676 A1 | 8/1988 |
| EP | 0447014 A2 | 9/1991 |
| EP | 0803250 A1 | 10/1997 |
| EP | 2075246 A1 * | 12/2007 |
| JP | H07509218 A | 10/1995 |
| JP | 2011511011 A | 4/2011 |
| JP | 2012533539 A | 12/2012 |
| WO | 1998031702 A1 | 7/1998 |
| WO | 2002072813 A1 | 9/2002 |
| WO | 2006010097 A2 | 1/2006 |
| WO | 2006111856 A1 | 10/2006 |
| WO | 2007078599 A2 | 7/2007 |
| WO | 2008128783 A2 | 10/2008 |
| WO | 2009134725 A2 | 11/2009 |
| WO | 2012083017 A2 | 6/2012 |
| WO | 2012087983 A1 | 6/2012 |
| WO | 2012122514 A1 | 9/2012 |
| WO | 2013016725 A1 | 1/2013 |
| WO | 2013052652 A1 | 4/2013 |
| WO | 2013086379 A3 | 8/2013 |
| WO | 2014093918 A1 | 6/2014 |
| WO | 2014164861 A1 | 10/2014 |
| WO | 2014197653 A2 | 12/2014 |
| WO | 2016154203 A1 | 9/2016 |

OTHER PUBLICATIONS

Zala et al. "Laboratory Techniques of purification and isolation," Int. J. Drug Dev. & Res., 2012, vol. 4, No. 2, pp. 41-455.*

Bergstrom et al. "Accuracy of calculated pH-dependent aqueous drug solubility," (European J. Pharmaceutical Sciences, 2004, vol. 22, pp. 387-398.*
International Search Report and Written Opinion dated Feb. 27, 2017 for International Patent Application No. PCT/US2016/066420.
Shi et al., "Antigen retrieval immunohistochemistry under the influence of pH using monoclonal antibodies", Journal of Histochemistry & Cytochemistry, Feb. 1, 1995, vol. 43(2), pp. 193-201.
Zukiwski et al., "Independent characterization by duel staining of progesterone receptor (PR) and estrogen receptor (ER) in breast cancer (BC)", Proc ASCO, abstract No. 118076 (2003).
Ferland "Synthetic Cardenolides and Related Products. III. Isocardenolides," Canadian Journal of Chemistry (1974) 52,, pp. 1642-1661.
Non-Final Office Action dated Nov. 27, 2018 in U.S. Appl. No. 15/825,697.
Graham, J. et al., "Expression and transcriptional activity of progesterone receptor A and progesterone receptor B in mammalian cells.", Breast Cancer Research (2002) 4(5):187-190.
Graham, J. et al., "Physiological action of progesterone in target tissues." Endocr Rev (1997) 18: 502-519.
Grunberg et al., "Long-Term Administration of Mifepristone (RU486): Clinical Tolerance During Extended Treatment of Meningioma", Cancer Investigation, Jun. 11, 2009, 24:8, pp. 727-733.
Guohua et al., "Synthesis of Progesterone Receptor Antagonist ZK98299," Zhongguo Yaoke Daxue Xuebao (1992), 23 (4), 209-12.
Hancock, B. et al., "Characteristics and Significance of the Amorphous State in Pharmaceutical Systems" Journal of Pharmaceutical Sciences (1997) vol. 88, No. I, pp. 1-12.
Heinz, S. et al., "Simple combinations of lineage-determining transcription factors prime cis-regulatory elements required for macrophage and B cell identities.", (2010) Mol Cell 38: 576-589.
Heydarzadeh et al., "Catalyst-free conversion of alkali cellulose to fine carboxymethyl cellulose at mild conditions", (2009) World Appl. Sci. J. 6 (4) 564-569.
Hopp, T. et al., "Breast Cancer Patients with Progesterone Receptor PR-A-Rich Tumors Have Poorer Disease-Free Survival Rates", Clin. Cancer Res. (2004) 10; 2751.
Hubler, T. et al., "Intronic hormone response elements mediate regulation of FKBP5 by progestins and glucocorticoids." (2004) Cell Stress Chaperones 9: 243-252.
Hurtado, A. et al., "FOXA 1 is a key determinant of estrogen receptor function and endocrine response." (2011) Nat Genet 43: 27-33.
Hutt, E. et al., "Clinical and pathological correlation of the activated form of the progesterone receptor (APR) in Endometrial Cancer (EC)", ECC 2013, 1.002.
International Search Report of International Patent Application No. PCT/US2012058732 dated Dec. 11, 2012.
International Application No. PCT/US2014/023651, Written Opinion dated Jul. 28, 2014, 11 pgs.
International Preliminary Report on Patentability issued in Internaional Patent Application No. PCT/IB2015/058369 dated May 2, 2017.
International Search Report and Written Opinion for International Patent Application No. PCT/US2017/023256 dated Jun. 16, 2017.
International Search Report and Written Opinion of PCT Application No. PCT/US2016/053435 dated Dec. 15, 2016.
International Search Report issued in International Patent Application No. PCT/IB2015/058369 dated Jan. 25, 2016.
International Search Report of corresponding PCT Application No. PCT/IB 2015/000312 dated Jul. 22, 2015.
International Search Report of PCT Application No. PCT/US2015/060940 dated Jan. 28, 2016.
Ishibashi, H. et al., "Progesterone receptor in non-small cell lung cancer—a potent prognostic factor and possible target for endocrine therapy", Cancer Res. (2005) 65 (14) 6450-8.
Jang et al, "Cytochrome P4503A4-Mediated N-Demethylation of the Antiprogestins Lilopristone and Onapristone", The American Society for Pharmacology and Experimental Therapeutics (1997) vol. 25, No. 10, 1119-1122.
Ji, H. et al., "An integrated software system for analyzing Ch IP-chip and ChIP-seq data." (2008) Nat Biotechnol 26: 1293-1300.

(56) References Cited

OTHER PUBLICATIONS

John, S. et al. "Chromatin accessibility pre-determines glucocorticoid receptor binding patterns.", (2011) Nat Genet 43: 264-268.
Jonat et al., "The clinical efficacy of progesterone antagonists in breast cancer", Endocrine Therapy of Breast Cancer, (2002) pp. 117-124.
Jonat, W. et al., "Randomized phase 2 study of lonaprisan as second line therapy for progesterone receptor positive breast cancer", Ann Oncol (2013) 24: 2543-2548.
Joseph, R. et al. "Integrative model of genomic factors for determining binding site selection by estrogen receptor-alpha." (2010) Mol Sys! Biol 6: 456.
Kamimura, H. et al., "Assessment of chimeric mice with humanized liver as a tool for predicting circulating human metabolites drug metab pharmacokinet", (2010) 25(3): 223-235.
Kao, L. et al., "Global gene profiling in human endometrium during the window of implantation." (2002) Endocrinology 143: 2119-2138.
Kawaguchi, Y. et al, "Drug and crystal polymorphism", Journal of Human Environmental Engineering, 2002, vol. 4, No. 2, p. 310-317.
Kim, J. et al., "Progesterone Action in Endometrial Cancer, Endometriosis, Uterine Fibroids, and Breast Cancer", Endocrine Rev. (2013) 34: 130-162.
Klijn et al., Progesterone antagonists and progesterone antagonist and progesterone receptor modulation in the treatment of beast cancer, (2000) Steroids, v. 65 pp. 825-830.
Knutson, et al., "Phosphorylated and sumoylation-deficient progesterone receptors drive proliferative gene signatures during breast cancer progession", Breast Cancer Research, 2012, vol. 14: R95.
Kocienski, Carbonyl Protecting Groups, 3rd Edition, Thieme (2005), pp. 58-59.
Koivisto-Korander, R. "Mifepristone as treatment of recurrent progesterone receptor-positive uterine leiomyosarcoma", Obstetrics and Gynecology (2007) 109: 512-514.
Kojima, T., "To improve efficiency of selecting crystal shape with drug development", Journal of Pharmaceutical Science and Technology, (2008) vol. 68, No. 5, p. 344-349.
Krum, S. et al., "Unique ERalpha cistromes control cell type-specific gene regulation." (2008) Molecular Endocrinology 22: 2393-2406.
Kushner, P. et al., "Estrogen receptor pathways to AP-1." (2000) J Steroid Biochem Mol Biol 74: 311-317.
Lanari, C. et al., "Antiprogestins in breast cancer treatment: are we ready?", Endocrine-Related Cancer (2012) 19: R35-R50.
Lange, C. et al., "Progesterone Receptor Action: Translating Studies in Breast Cancer Models to Clinical Insights", Innov Endocrinol Cancer (2008) 7: 94-110.
Langmead, B. et al., "Ultrafast and memory-efficient alignment of short DNA sequences to the human genome" (2009) Genome Biol 10: R25.
Lasonos, A. et al., "Scientific Review of Phase I Protocols With Novel Dose-Escalation Designs: How Much Information is Needed?", Journal of Clinical Oncology (2015) JCO. 2014.59. 8466.
Lieberman, B. et al., "The constitution of a progesterone response element." (1993) Mol Endocrinol 7: 515-527.
Liu, Z. et al., "Sequential recruitment of steroid receptor coactivator-1 (SRC-1) 5 and p300 enhances progesterone receptor-dependent initiation and reinitiation of transcription from chromatin." (2001) Proc Natl Acad Sci U S A 98: 12426-12431.
Longacre, T. "A correlative morphologic study of human breast and endometrium in the menstrual cycle." (1986) Am J Surg Pathol 10: 382-393.
Lupien, M. et al., "FoxA 1 translates epigenetic signatures into enhancer-driven lineage-specific transcription." (2008) Cell 132: 958-970.
Macquarrie, K. et al., "Genome-wide transcription factor binding: beyond direct target regulation." (2011) Trends Genetics 27: 141-148.

McGowan et al., "Cytoskeletal Responsiveness to Progestins is Dependent on Progesterone Receptor A Levels," Journal of Molecular Endocrinology, 2003, 31, pp. 241-253.
McKenna, N. et al., "Combinatorial control of gene expression by nuclear receptors and coregulators." (2002) Cell 108: 465-474.
Metzger, E. et al., "LSD1 demethylates repressive histone marks to promote androgen-receptor-dependent transcription.", Nature (2005) 437:436-439.
Meuleman et al., "Morphological and Biochemical Characterization of a Human Liver in a uPA-SCID Mouse Chimera", Hepatology (2005) 41 (4); 847-856.
Mortazavi, A. et al., "Mapping and quantifying mammalian transcriptomes by RNA-Seq.", (2008) Nat Methods 5: 621-628.
Mortel, R. el al., "Heterogeneity and Progesterone—Receptor Distribution in Endometrial Adenocarcinoma", Cancer (1984) 53:113-116.
Mote et al. "Detection of progesterone receptor forms A and B by immunohistochemical analysis", (2001) J. Clin. Pathol. 54: 624-630.
Mote, P. "Relative expression of progesterone receptors A and Bin premalignant and invasive breast lesions", Breast Cancer Research (2000) 2 (Suppl 1) P2.01 doi:I 0.1186/bcrl 03.
Mote, P. et al., "Loss of co-ordinate expression of progesterone receptors A and B is an early event in breast carcinogenesis", Breast Cancer Res Treat (2002) 72(2): 163-72.
Mote, P. et al., "Progesterone receptor isoforms in normal and malignant breast", Ernst Schering Found Symp Proc. (2007) (1):77-107.
Murtagh, J. et al., "The Nuclear Factor I (NFI) gene family in mammary gland development and function.", (2003) J Mammary Gland Biol Neoplasia 8: 241-254.
Nadji, M. "Immunohistochemistry of Estrogen and Progesterone Receptors Reconsidered: Experience With 5,993 Breast Cancers", Anatomic Pathol. (2005) 123: 21-27.
Neef et al., "New Steroids by Simmons-Smith Methyenation and Subsequent Rearrangement", J_ Org_ Chem., (1987) vol. 52, No. 18 pp. 4143-4146.
Nelson, C. et al., "Determinants of DNA sequence specificity of the androgen, progesterone, and glucocorticoid receptors: evidence for differential steroid receptor response elements." (1999) Mol Endocrinol 13: 2090-2107.
Non-Final Office Action dated Mar. 6, 2015 in U.S. Appl. No. 14/205,694.
Notice of Allowance received in U.S. Appl. No. 15/825,697, dated Aug. 9, 2018.
Onate, S. et al., "Sequence and characterization of a coactivator for the steroid hormone receptor superfamily." (1995) Science 270: 1354-1357.
Pearson, P. Wienkers, editors. Handbook of drug metabolism:, New York: Informa Healthcare; 2009. pp. 445-464.
Pierrou, S. et al., "Cloning and characterization of seven human forkhead proteins: binding site specificity and DNA bending." (1994) EMBO J 13: 5002-5012.
Press, M. et al. "Comparison of different antibodies for detection of progesterone receptor in breast cancer", Steroids (2002) 67:799-813.
Puma, et al., Dimensionless analysis of slurry photocatalytic reactors using two-flux and six-flux radiation absorptionscattering models, Catalysis Today, 2007, 122, pp. 78-90.
Puma, G. L., "Photocatalytic oxidation of multicomponent systems of herbicides: scale-up of laboratory kinetics rate data to plant scale" Catal. Today 2007, 124-132.
Rayasam, G. et al., "Ligand-specific dynamics of the progesterone receptor in living cells and during chromatin remodeling in vitro.", Mol Cell (2005) Biol 25: 2406-2418.
Reddy, T. et al. "Genomic determination of the glucocorticoid response reveals unexpected mechanisms of gene regulation." (2009) Genome Res 19: 2163-2171.
Reich, M. et al. (2006) GenePattern 2.0. Nat Genet 38: 500-501.
Rezai et al., "A single-dose PK study of onapristone including the effect of food on absorption", Cancer Chemother. Pharmacol. (2015) 76: 171-177.

(56) References Cited

OTHER PUBLICATIONS

Rezai, K. et al., "Population pharmacokinetic (PPK) modeling of onapristone in patients (pts) with progesterone receptor (PR)-expressing cancers", AACR Annual Meeting (2015) Abstract 4523.
Richer, J. et al., "Differential gene regulation by the two progesterone receptor isoforms in human breast cancer cells." (2002) J Biol Chem 277: 5209-5218.
Robertson et al. "Onapristone, a progesterone receptor antagonist, as first-line therapy in primary breast cancer", (1999) vol. 35, Issue 2, pp. 214-218.
Roschke, A. et al., "Karyotypic complexity of the NCI-60 drug-screening panel." (2003) Cancer Res 63: 8634-8647.
Rossouw, J. et al., Risks and benefits of estrogen plus progestin in healthy postmenopausal women: principal results from the Women's Health Initiative randomized controlled trial. (2002) JAMA 288: 321-333.
Scarpin, K. et al., "Progesterone action in human tissues: regulation by progesterone receptor (PR) isoform expression, nuclear positioning and coregulator expression." (2009) Nucl Recept Signal 7: e009.
Schlogl S. et al., "Characteristics of the photochemical prevulcanization in a falling film photoreactor" J. App. Polymer Science, 2012, 124, 3478-3486.
Search Report of International Patent Application No. PCT/US2012/058732 dated Dec. 11, 2012.
Search Report of International Patent Application No. PCT/US2015/024792, dated Aug. 7, 2015.
So, A. et al., "Determinants of cell- and gene-specific transcriptional regulation by the glucocorticoid receptor." PLoS Genetics (2007) vol. 3, Issue 6; 0927-0938.
Streuli, C. et al., "Stat5 as a target for regulation by extracellular matrix.", (1995) J Biol Chem 270: 21639-21644.
Tang, Q. et al., "A comprehensive view of nuclear receptor cancer cistromes." (2011) Cancer Res 71: 6940-6947.
Telleria et al., "Antiprogestins in Ovarian Cancer. Ovarian Cancer—Clinical and Therapeutic Perspectives, DOI: 10.5772/25269", (2012) 207-230.
Thike et al., "Triple-negative breast cancer; clnicopathological characteristics and relationship with basal-like breast cancer," Modern Pathology, 2010; 23; pp. 123-133.
Tseng, L. et al., "Progesterone receptor (hPR) upregulates the fibronectin promoter activity in human decidual fibroblasts." (2003) DNA Cell Biol 22: 633-640.
Vicent, G. et al., "Chromatin remodeling and control of cell proliferation by progestins via cross talk of progesterone receptor with the estrogen receptors and kinase signaling pathways." (2006) Ann N Y Acad Sci 1089: 59-72.
Vicent, G. et al., "Minireview: role of kinases and chromatin remodeling in progesterone signaling to chromatin." Mol Endocrinol (2010) 1-11.
Vicent, G. et al., "Two chromatin remodeling activities cooperate during activation of hormone responsive promoters." PLoS Genet (2009) vol. 5, Issue 7: 1-13.
Vicent, G. et al., Nuclear factor 1 synergizes with progesterone receptor on the mouse mammary tumor virus promoter wrapped around a histone H3/H4 tetramer by facilitating access to the central hormone-responsive elements. (2010) J Biol Chem 285: 2622-2631.
Wang, D. et al. "Reprogramming transcription by distinct classes of enhancers functionally defined by eRNA." Nature (2011)1-25.
Wang, Q. et al., A hierarchical network of transcription factors governs androgen receptor-dependent prostate cancer grow1h. (2007) Mol Cell 27: 380-392.
Welboren, W. et al., "ChIP-Seq of ERalpha and RNA polymerase II defines genes differentially responding to ligands." (2009) EMBO J 28: 1418-1428.
Written Opinion for PCT/US2017/023256, dated Jun. 16, 2017.
Written Opinion issued in International Patent Application No. PCT/IB32015/058369 dated Jan. 25, 2016.
Written Opinion of International Patent Application No. PCT/US2012/058732, dated Dec. 11, 2012.
Yamano, M., "Approach to Crystal Polymorph in Process Research of New Drug", Journal of Synthetic Organic Chemistry, (2007) vol. 65, No. 9, p. 907(69)-913(75).
Yin, P. et al. "Genome-wide progesterone receptor binding: cell type-specific and shared mechanisms in T47D breast cancer cells and primary leiomyoma cells." (2012) PLoS One 7: e29021.
Yin, P. et al., "Transcription Factor KLFI 1 Integrates Progesterone Receptor Signaling and Proliferation in Uterine Leiomyoma Cells", Cancer Res. (2010) 70(4); 1722-30.
Ace, C. et al., "Microarray profiling of progesterone-regulated endometrial genes during the rhesus monkey secretory phase." (2004) Reprod Biol Endocrinol 2: 54.
Ariga, N. et al: "Progesterone receptor A and B isoforms in the human breast and its disorders", (2001) Jpn J. Cancer Res. vol. 92, No. 3.
Arnett-Mansfield, et al., "Focal Subnuclear Distribution of Progesterone Receptor is Ligand Dependent and Associated with Transcriptional Activity," Mol Endocrinol, Jan. 2007, vol. 2, No. 1, pp. 14-29.
Arnett-Mansfield, et al., "Subnuclear Distribution of Progesterone Receptors A and B in Normal and Malignant Endometrium", J Clin Endocrinol Metab, (2004) vol. 89, No. 3, pp. 1429-1442.
Bailey, T. et al., "MEME: discovering and analyzing DNA and protein sequence motifs." (2006) Nucleic Acids Res 34: W369-373.
Bailey, T., et al., "The value of position-specific priors in motif discovery using MEME." (2010) BMC Bioinformatics 11: 179.
Baillie et al., "Role of Biotransformation in Drug-Induced Toxicity: Influence of Intra-and Inter-Species Differences in Drug Metabolism", (2011) 26(1): 15-29.
Ballare, C. et al., "Nucleosome-Driven Transcription Factor Binding and Gene Regulation." (2013) Molecular Cell 49, 1-13.
Bamberger et al. "Progesterone receptor isoforms, PR-Band PR-A, in breast cancer: Correlations with clinicopathologic tumor parameters and expression of AP-1 factors", Horm Res (2000) CH. vol. 54: 32-37.
Beck, C. A. et al., "Two Types of Anti-progestins Have Distinct Effects on Site-specific Phosphorylation of Human Progesterone Receptor", The Journal of Biological Chemistry (1996) 271: 1209-1217.
Beguelin, W. et al., "Progesterone receptor induces ErbB-2 nuclear translocation to promote breast cancer grow1h via a novel transcriptional effect: ErbB-2 function as a coactivator of Stat3." (2010) Mol Cell Biol 30: 5456-5472.
Belikov, S. et al., "FoxA 1 binding directs chromatin structure and the functional response of a glucocorticoid receptor-regulated promoter." (2009) Mol Cell Biol 29: 5413-5425.
Benagiano, G. et al., "Selective progesterone receptor modulators 3: use in oncology, endocrinology and psychiatry", Expert Opin. Pharmacother (2008) 9:2487-2496.
Beral, V. et al., "Breast cancer and hormone-replacement therapy in the Million Women Study." (2003) Lancet 362: 419-427.
Beral, V. et al., "Breast Cancer Risk in Relation to the Interval Between Menopause and Starting Hormone Therapy." (2011) J Natl Cancer Inst 103: 296-305.
Bernardo, G. et al., FOXA1 is an essential determinant of ERalpha expression and mammary ductal morphogenesis. (2010) Development 137: 2045-2054.
Blankenstein, M. et al., "Occurrence, regulation, and significance of progesterone receptors in human meningiome", Steroids (2000) 65: 795-800.
Bolton, C. et al. "Cell- and gene-specific regulation of primary target genes by the androgen receptor.", (2007) Genes Dev 21: 2005-2017.
Bonkhoff, H. et al., "Progesterone Receptor Expression in Human Prostate Cancer: Correlation With Tumor Progression. Prostate" (2001) 48: 285-291.
Bonneterre et al., "Abstract P5-02-13: Triple negative breast cancer the impact of isotype-specific progesterone receptor antibodies on the diagnosis results Cancer Researeh", (2015) vol. 75; 9, pp. P5-02-P5-13, 1538-7445.
Bonneterre, J. et al., "Development of a technique to detect the activated form of the progesterone receptor and correlation with clinical and histopathological characteristics of endometrioid

(56) References Cited

OTHER PUBLICATIONS adenocarcinoma of the uterine corpus", Gynecologic Oncology (2015) doi: 10.1016/j.ygyno.2015.06.037.
Borthwick, J. et al., "Determination of the transcript profile of human endometrium.", (2003) Mol Hum Reprod 9: 19-33.
Bravieri, R. et al., "Different DNA contact schemes are used by two winged helix proteins to recognize a DNA binding sequence." (1997) Nucleic Acids Res 25: 2888-2896.
Cameron, S. et al, "Critchley HOD, Buckley CH et al. The effects of post-ovulatory administration of onapristone on the development of a secretory endometrium", Human Reproduction (1996) 11 (1):40-49.
Cameron, S. et al., "Effects of onapristone on postmenopausal endometriurn. Steroids", (2003) 68: 1053-1059.
Cantillo (Kappe) et al. "A Continuous-Flow Protocol for Light-Induced Benzylic Fluorinations" J. Org. Chem., 2014, 79 (17), pp. 8486-8490.
Carroll, J. et al., "Genome-wide analysis of estrogen receptor binding sites." (2006) Nat Genet 38: 1289-1297.
Chapman et al., "GenePattern 2.0; Nature Genetics" Nature Publishing Group (2006); vol. 38, No. 5.
Chlebowski, R. et al., "Estrogen plus progestin and breast cancer incidence and mortality in postmenopausal women." (2010) JAMA 304: 1684-1692.
Cicatiello, L. et al., "Estrogens and progesterone promote persistent CCND1 gene activation during G1 by inducing transcriptional derepression via c-Jun/c-Fos/estrogen receptor (progesterone receptor) complex assembly to a distal regulatory element and recruitment of cyclin D1 to its own gene promoter." (2004) Mol Cell Biol 24: 7260-7274.
Cirillo LA, Zaret KS (2007) Specific interactions of the wing domains of FOXA1 transcription factor with DNA. J Mol Biol 366: 720-724.
Clarke, C. et al., "Monoclonal antibodies to human progesterone receptor: characterization by biochemical and immunohistochemical techniques." (1987) Endocrinology 121: 1123-1132.
Clarke, C. et al., "Non-Overlapping Progesterone Receptor Cistromes Contribute to Cell-Specific Transcriptional Outcomes." (2012) PLoS One 7(4): e35859. doi:10.1371/journal.pone.0035859.
Clarke, C. et al., "Progestin regulation of cellular proliferation." (1990) Endocr Rev 11: 266-301.
Cottu, P. et al., "Onapristone (ONA) in progesterone receptor (PR)-expressing tumors: Efficacy and biomarker results of a dose-escalation phase 1 study", J. Clin. Oncol. (2015) 33 (suppl; abstr 5593).
Croxatto, H. et al., "Effect of the antiprogestin onapristone on follicular growth in women", Human Reproduction (1994) 9: 1442-1447.
EP15776251.9 partial supplementary European search report (R 164 EPC) dated Nov. 7, 2017.
Etreby, et al., "Antitumor Activity of Mifepristone in the Human LNCaP, LNCaP-C4, and LNCaP-C4-2 Prostate Cancer Models in Nude Mice", The Prostate, 2000, vol. 42, No. 2, pp. 99-106.
Examination Report of Australian Patent Application 2012318618, dated Aug. 9, 2016.
Examination Report of New Zealand Patent Application No. 623140 dated Dec. 8, 2014.
Extended European Search Report of European Patent Application No. 12837954.2 dated Apr. 17, 2015.

Faivre, E et al., "Progesterone receptor rapid signaling mediates serine 345 phosphorylation and tethering to specificity protein 1 transcription factors." (2008) Mol Endocrinol 22: 823-837.
Friedman, J. et al., "The Foxa family of transcription factors in development and metabolism." (2006) Cell Mol Life Sci 63: 2317-2328.
Garcia-Bassets, I. et al., "Histone methylation-dpendent mechanisms impose ligand dependency for gene activation by nuclear receptors." (2007) Cell 128: 505-518.
Goyeneche, A. et al., "Antiprogestins in gynecological diseases" Reproduction (2015) 149: RI5-R33.
Graham, D. et al., "Determination of the activated form of the progesterone receptor (PR) in endometrial cancer (EC)", J. Clin. Oncol. (2013); 3J (suppl; abstr 5602).
Graham, J. "Progesterone receptors—animal models and cell signaling in breast cancer Expression and transcriptonal activity of progesterone receptor A and progestereone receptor B in mamalian cells", Breast Cancer Res (2002) 4: 187-190.
Graham, J. et al., "Altered progesterone receptor isoform expression remodels progestin responsiveness of breast cancer cells." (2005) Mol Endocrinol 19: 2713-2735.
Graham, J. et al., "Characterization of progesterone receptor A and B expression in human breast cancer." (1995) Cancer Res 55: 5063-5068.
Graham, J. et al., "DNA replication licensing and progenitor numbers are increased by progesterone in normal human breast." (2009) Endocrinology 150: 3318-3326.
Gwin K., et al., "Breast carcinoma with chondroid differentiation:a clinicopathologic study of 21 triple negative (ER-,PR-,Her2/neu-)cases." Int J Surg Pathol. (2010) 8 (1):27-35.
Non-Final Office Action dated Feb. 19, 2019 in U.S. Appl. No. 15/464,085.
Non-Final Office Action dated Jan. 23, 2019 in U.S. Appl. No. 14/681,032.
Notice of Allowance received in U.S. Appl. No. 15/274,555 dated Jan. 15, 2019.
U.S. Appl. No. 15/274,555, filed Sep. 23, 2016, which claims priority to U.S. Appl. No. 62/233,166, filed Sep. 25, 2015.
U.S. Appl. No. 15/464,085, filed Mar. 20, 2017, which claims priority to U.S. Appl. No. 62/310,944, filed Mar. 21, 2016.
U.S. Appl. No. 15/825,697, filed Nov. 29, 2017, which claims priority to U.S. Appl. No. 62/428,401, filed Nov. 30, 2016.
U.S. Appl. No. 14/661,382, filed Mar. 18, 2015, which is a divisional of U.S. Appl. No. 14/203,814, filed Mar. 11, 2014; now granted U.S. Pat. No. 9,193,757, which claims priority to U.S. Appl. No. 61/777,751, filed Mar. 12, 2013.
U.S. Appl. No. 16/382,741, filed Apr. 12, 2019, which is a continuation of U.S. Appl. No. 15/274,555, filed Sep. 23, 2016, which claims priority to U.S. Appl. No. 62/233,166, filed Sep. 25, 2015.
U.S. Appl. No. 14/645,111, filed Mar. 11, 2015, which claims priority to U.S. Appl. No. 61/951,650, filed Mar. 12, 2014.
U.S. Appl. No. 14/205,694, filed Mar. 12, 2014, which claims priority to U.S. Appl. No. 61/779,720, filed Mar. 13, 2013.
U.S. Appl. No. 14/681,032, filed Apr. 7, 2015, which claims priority to U.S. Appl. No. 61/976,872, filed Apr. 8, 2014.
U.S. Appl. No. 14/698,100, filed Apr. 28, 2015, which is a continuation of U.S. Appl. No. 13/644,872, filed Oct. 4, 2012 which claims priority to U.S. Appl. No. 61/542,931, filed Oct. 4, 2011.
U.S. Appl. No. 14/942,809, filed Nov. 16, 2015, which claims priority to U.S. Appl. No. 62/080,868, filed Nov. 17, 2014.

* cited by examiner

AMORPHOUS ONAPRISTONE COMPOSITIONS AND METHODS OF MAKING THE SAME

PRIORITY CLAIM

This application claims priority to U.S. Provisional Patent Application Ser. No. 62/267,540, filed Dec. 15, 2015. The above referenced application is incorporated herein by reference as if restated in full.

All references cited herein, including but not limited to patents and patent applications, are incorporated by reference in their entirety.

BACKGROUND

Onapristone (ONA) ((8S,11R,13R,14S,17S)-11-[4-(dimethylamino)phenyl]-17-hydroxy-17-(3-hydroxypropyl)-13-methyl-1,2,6,7,8,11,12,14,15,16-decahydrocyclopenta[a]phenanthren-3-one) is an anti-progestin drug and progesterone receptor antagonist has the following structure:

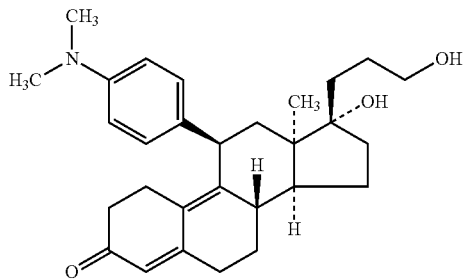

Onapristone is known to be an amorphous compound. For example, Onapristone has previously been isolated as an amorphous solid and as a yellow oil. Neef, et al. Steroids, 1984, 44, 349; Neef, et al., DE3321826. In contrast to onapristone, (3-Acyloxypropyl)-derivatives of onapristone were identified as crystalline. See U.S. Pat. No. 4,780,461. Recently, however, crystalline forms of onapristone have been identified. See, e.g., U.S. Patent Publication Number 2014/0271819.

The term "amorphous," as used herein, refers to the non-crystalline form of a chemical compound. Whereas the crystalline forms of a compound are characterized by structures assembled by the repetitive building up of fundamental units containing the molecules of the compound (known as unit cells), amorphous compounds have no such long-range repetitive structure, and are characterized by short-range, random ordering. Consequently, the lack of crystalline structure inherent to an amorphous compound may lead to significant differences in the physical and chemical properties of the compound, such as its solubility, dissolution rate, stability, bioavailability, and efficacy.

The amorphous form of a drug substance can be compared to crystalline forms of the compound using by a variety of techniques including, but not limited to, melting point, thermogravimetric analysis (TGA), differential scanning calorimetry (DSC), X-ray powder diffraction (XRPD), high performance liquid chromatography (HPLC), Raman microscopy, FT-IR spectroscopy, and solid-state nuclear magnetic resonance (ssNMR). The physical stability of the amorphous form of a compound can be measured, for example, under conditions where the temperature and humidity in the environment are controlled for various time periods.

The term "co-precipitate" refers to the simultaneous precipitation of more than one compound together in a single-phase solid form from a solution. The term "precipitate" refers to the formation of a solid from a liquid solution. Precipitates can be used, for example, to modulate the properties of a chemical compound (e.g., bioavailability, pharmacokinetics, stability).

SUMMARY

Aspects disclosed herein provide amorphous onapristone compositions and methods of making amorphous onapristone including, for example, by (1) pH cycling, (2) solvation-desolvation, (3) spray-drying onapristone/polymer mixtures, (4) solution-coprecipitation, and (5) solidification of hot melts.

One aspect provides methods of making amorphous onapristone by "pH cycling". In this procedure, onapristone bulk drug substance is dissolved in a solvent, decreasing the pH of the resulting solution to dissolve the compound, and subsequently increasing the pH of the resulting solution to form an amorphous precipitate.

Another aspect provides methods of making amorphous onapristone by dissolving onapristone in a suitable solvent, followed by evaporation of the solution to yield a solvate, and then desolvating the solvate under controlled conditions to yield amorphous drug substance.

Further aspects provide compositions comprising amorphous onapristone and polymeric excipients. These compositions may be obtained, for example, spray-drying or precipitation from a solution.

Yet another aspect provides methods of making amorphous onapristone by a "hot melt" process, whereby onapristone and various polymers are heated to form a polymer melt where the onapristone is dissolved in the resulting mixture. The melt is subsequently cooled to obtain the composition. Compositions comprising onapristone and various polymers are also provided.

As described herein, amorphous onapristone can be prepared as a pure drug substance, either through the use of a pH-cycling method or by controlled desolvation of the methanol solvate of onapristone. The pH-cycled product remains amorphous for extended periods of time. For example, the pH-cycled product has been shown to remain amorphous for at least 16.5 months, while the solvation-desolvation product was shown to remain amorphous for at least 29 weeks (i.e., 7.25 months).

When spray-dried along with appropriate polymeric excipients, onapristone can be obtained in the form of an amorphous dispersion at a 25% w/w drug loading level. Two such dispersions have been shown to remain amorphous for at least 15 months.

When processed using a hot-melt procedure together with appropriate polymeric excipients, onapristone can be obtained in the form of an amorphous dispersion at a nominal 25% w/w drug loading level. Seven such dispersions have been shown to remain amorphous for at least 8 weeks (i.e., two months).

Amorphous onapristone compositions as described herein, and made according to methods described herein, are stable in their amorphous state and retain their amorphous properties when stored under ambient conditions.

FIGURES

Figure 8:
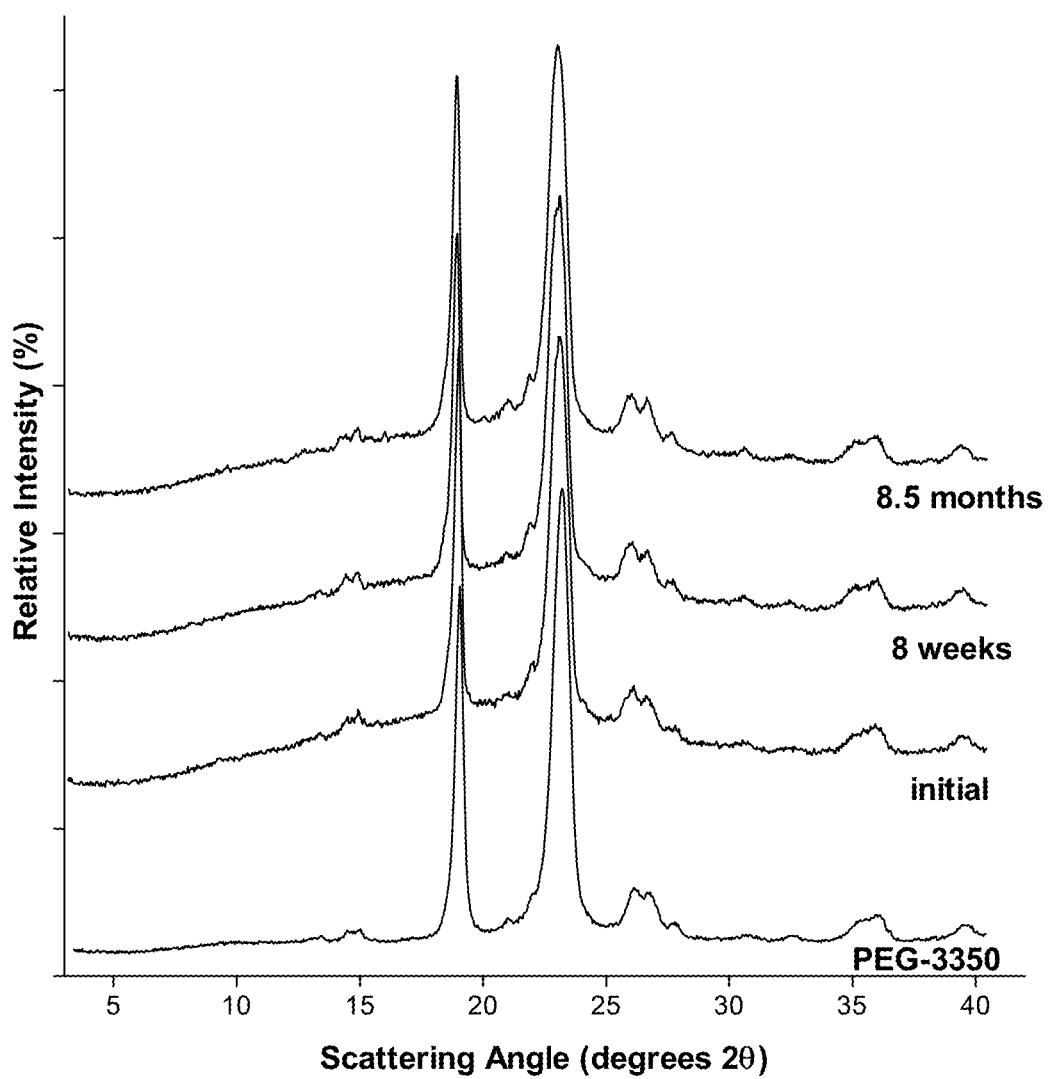
Figure 9:
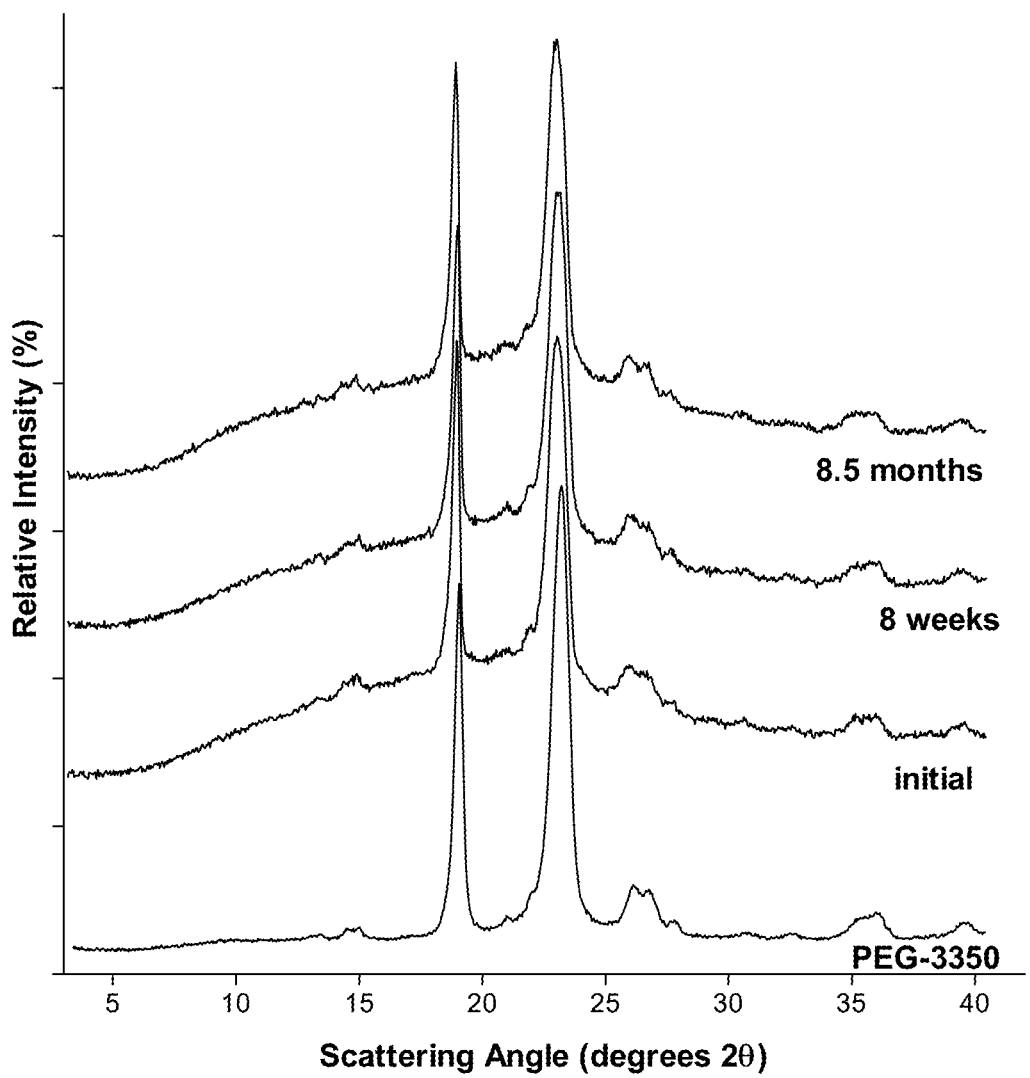
Figure 10:
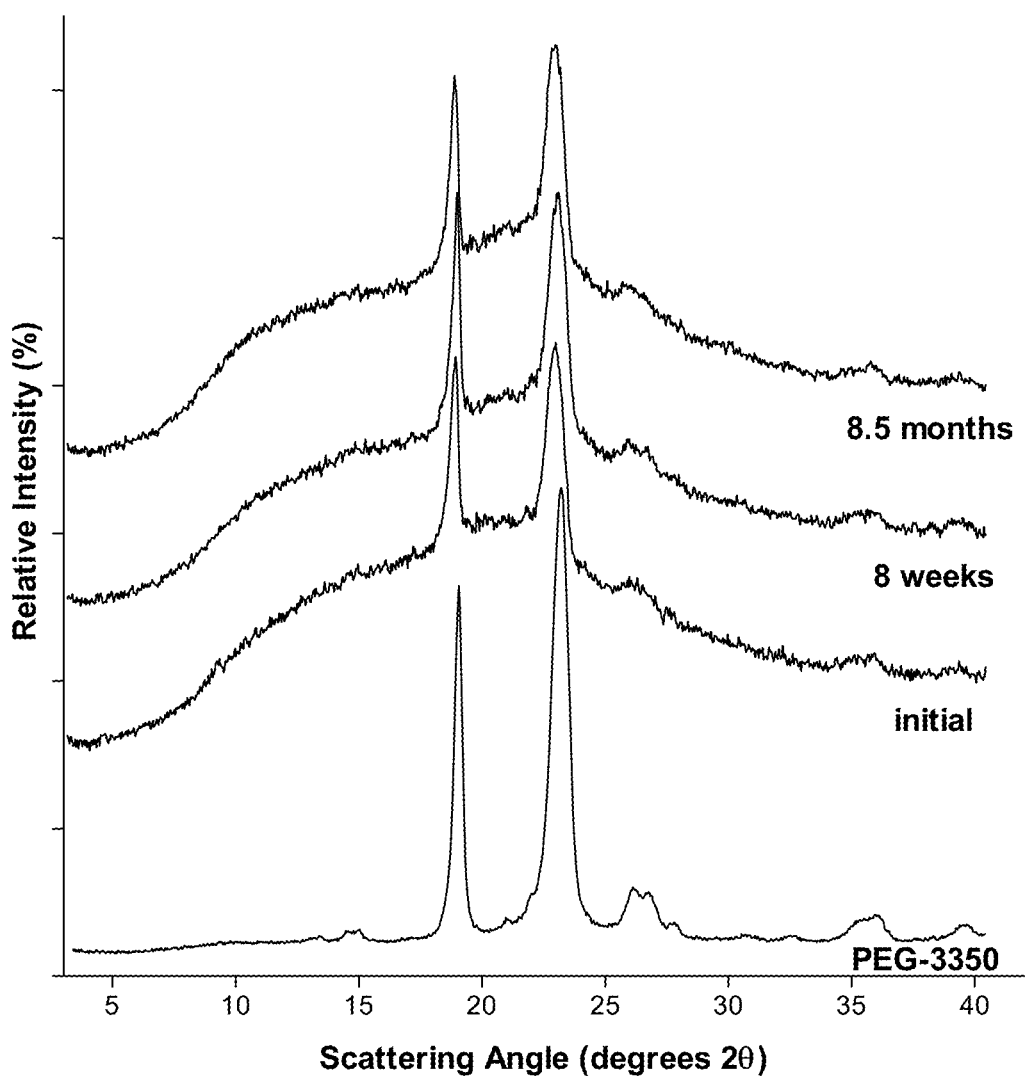
Figure 11:
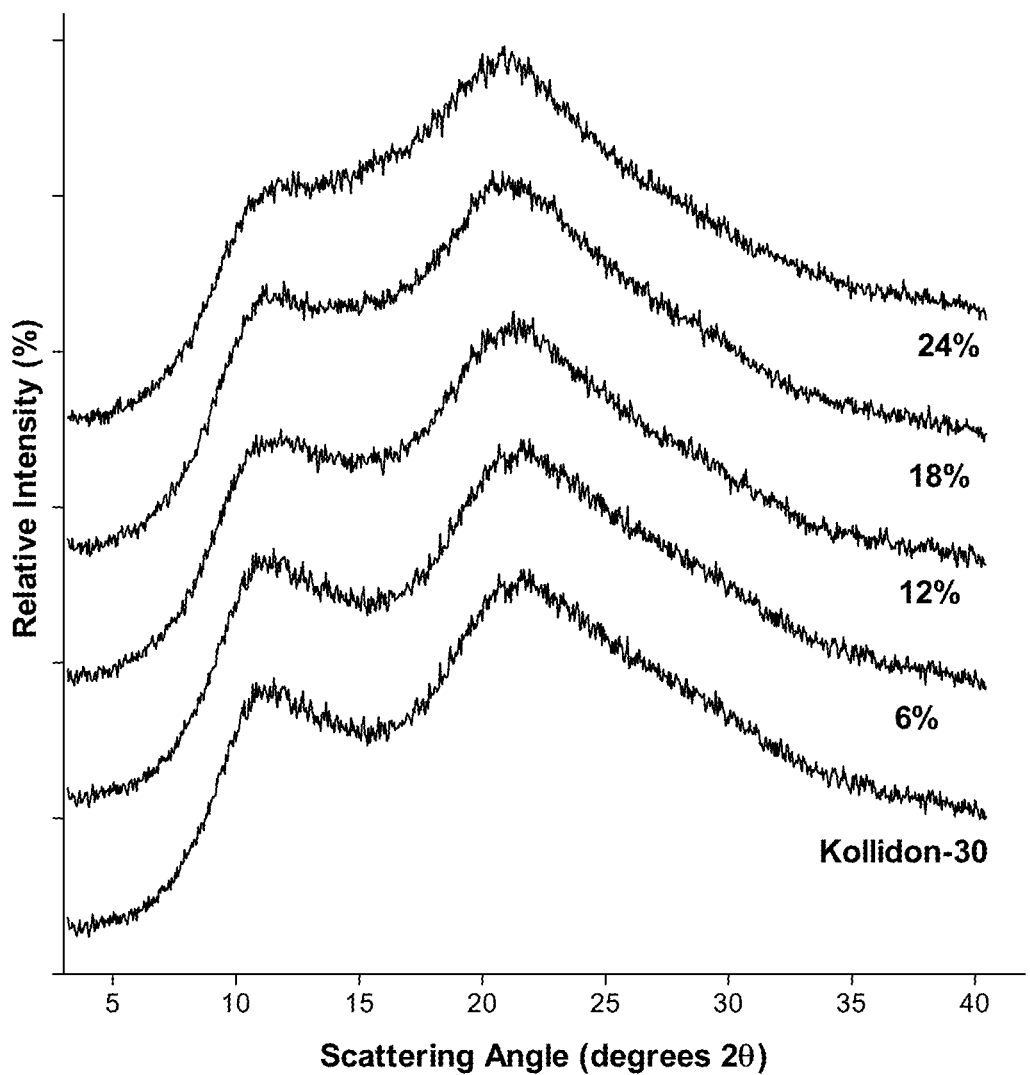
Figure 12:
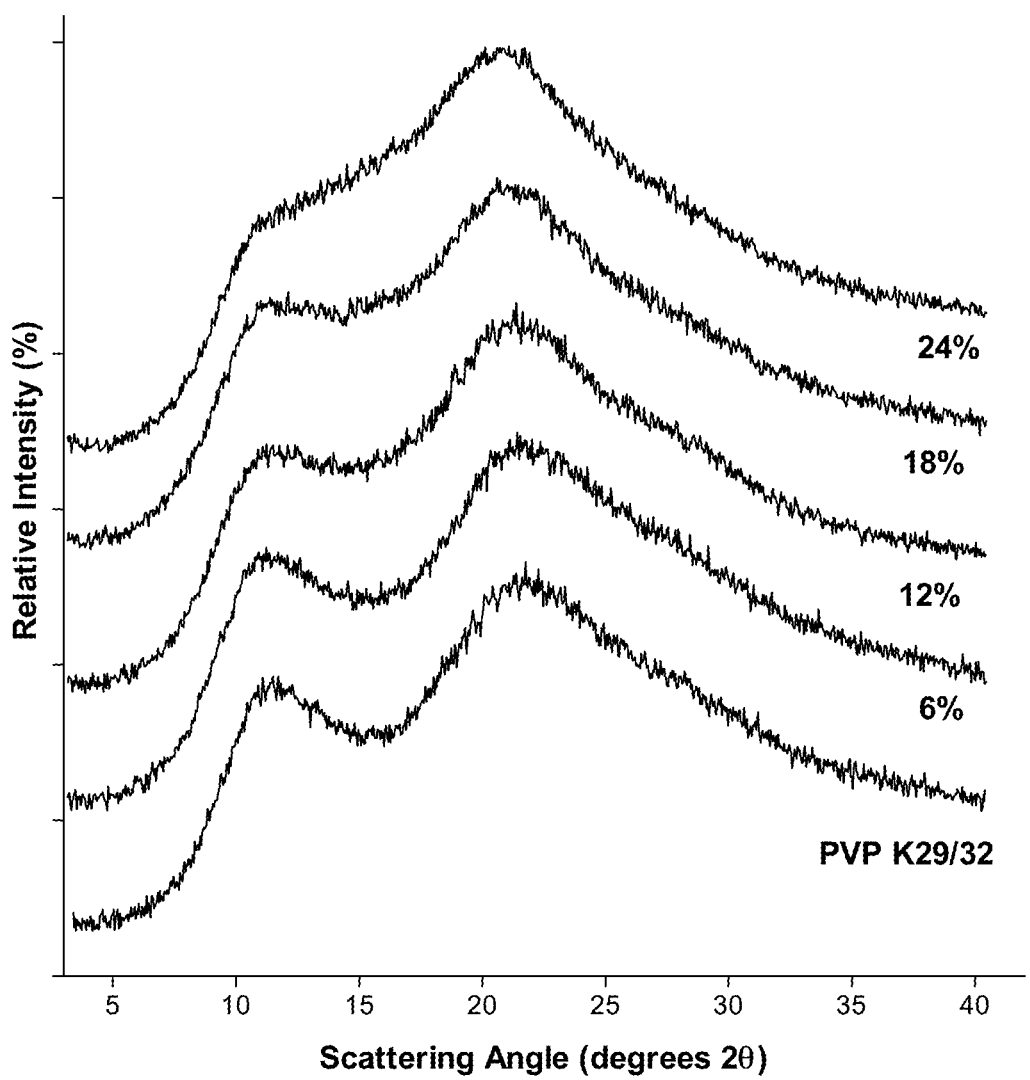
Figure 13:
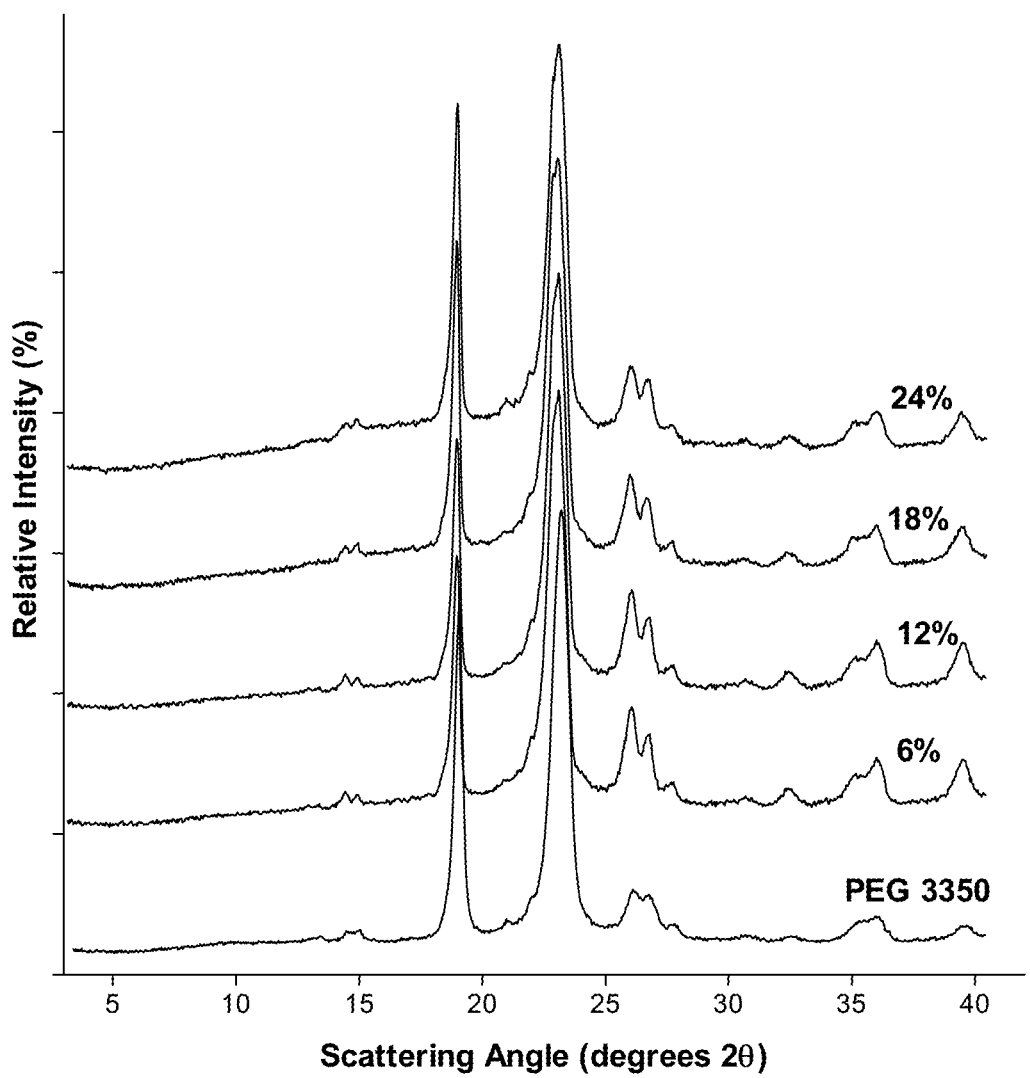
Figure 14:
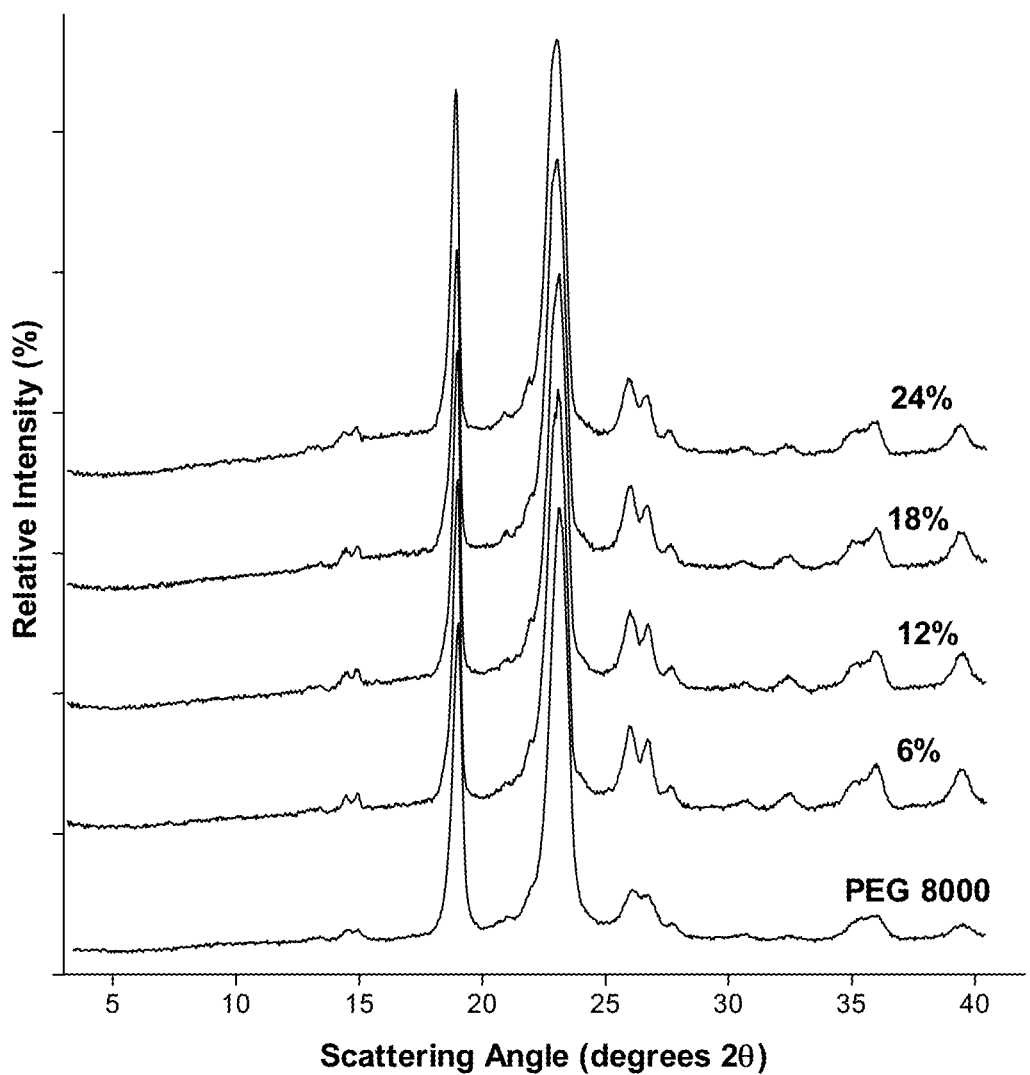
Figure 15:
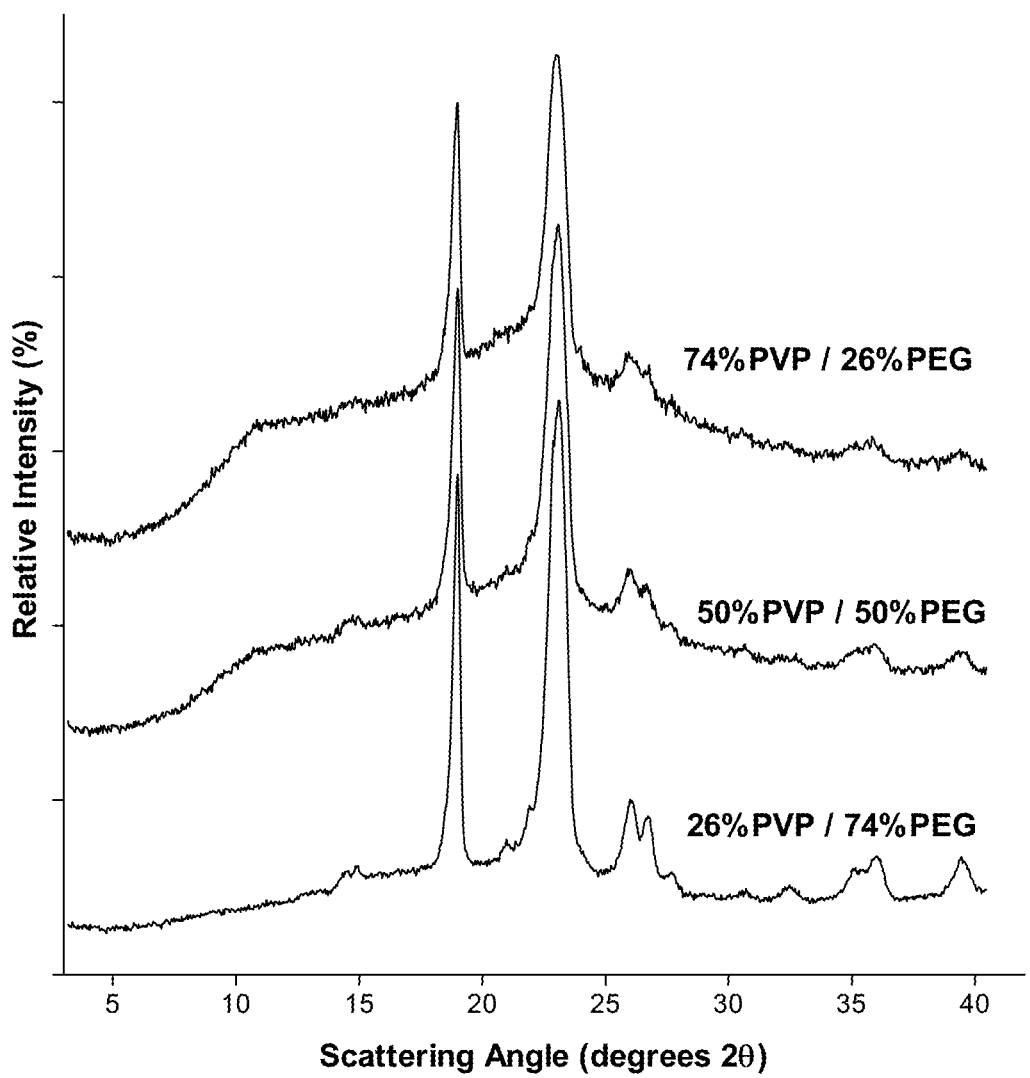

FIG. 8 shows exemplary X-ray powder diffraction patterns of approximately 25% w/w onapristone dispersions (containing 27.1% w/w polyvinyl pyrrolidone K29/32 and 72.9% w/w polyethylene glycol 3350) produced by the hot-melt method, and stored for various time periods;

FIG. 9 shows exemplary X-ray powder diffraction patterns of approximately 25% w/w onapristone dispersions (containing 49.3% w/w polyvinyl pyrrolidone K29/32 and 50.7% w/w polyethylene glycol 3350) produced by the hot-melt method, and stored for various time periods;

FIG. 10 shows exemplary X-ray powder diffraction patterns of approximately 25% w/w onapristone dispersions (containing 73.5% w/w polyvinyl pyrrolidone K29/32 and 26.5% w/w polyethylene glycol 3350) produced by the hot-melt method, and stored for various time periods;

FIG. 11 shows exemplary X-ray powder diffraction patterns of binary onapristone dispersions containing Kollidon® 30 produced by the solution-phase coprecipitate method, prepared to contain varying amounts of onapristone;

FIG. 12 shows exemplary X-ray powder diffraction patterns of binary onapristone dispersions containing polyvinylpyrrolidone K29/32 produced by the solution-phase coprecipitate method, prepared to contain varying amounts of onapristone;

FIG. 13 shows exemplary X-ray powder diffraction patterns of binary onapristone dispersions containing polyethylene glycol 3350 produced by the solution-phase coprecipitate method, prepared to contain varying amounts of onapristone;

FIG. 14 shows exemplary X-ray powder diffraction patterns of binary onapristone dispersions containing polyethylene glycol 8000 produced by the solution-phase coprecipitate method, prepared to contain varying amounts of onapristone; and FIG. 15 shows exemplary X-ray powder diffraction patterns of approximately 25% onapristone ternary dispersions containing various amounts of Kollidon® 30 and polyethylene glycol 8000 produced by the solution-phase coprecipitate method.

DETAILED DESCRIPTION

Before describing several exemplary aspects described herein, it is to be understood that the invention is not limited to the details of construction or process steps set forth in the following description and examples. The aspects described herein are capable of being practiced or being carried out in various ways. All publications, patents, and patent applications cited herein are incorporated by reference in their entirety.

Aspects described herein provide amorphous forms of onapristone which have advantageous properties including but not limited to increased bioavailability, increased stability, increased dissolution rate, and increased solubility. In one aspect, these properties relate to properties that will impart advantages with respect to formulating onapristone into a suitable dosage form.

Amorphous forms of onapristone have varying physical and chemical properties with respect, for example, solubility, melting temperature, and hygroscopicity, which may affect the stability of a particular dosage form of onapristone. Drug formulation and dosage form selection have a significant impact on the cost of manufacturing. Physical properties such as flow, particle size, surface area, and hardness may significantly impact the pharmacokinetics of the drug. For example, the dissolution and subsequent absorption of the drug in the body will affect the maximum concentration in the blood, clearance of the drug, and whether the drug is resident in the body for the optimal period of time.

In one aspect, amorphous onapristone is formed by adding onapristone to water, dissolving the onapristone in the water by adding one equivalent of an acid solution, and subsequently increasing the pH of the solution by the addition of one equivalent of base. At the end of this process, an amorphous precipitate is formed which may be isolated and characterized. In another aspect, the XPRD pattern of the precipitated onapristone does not produce any substantially sharp scattering peaks. The presence of a crystalline substance is indicated by the presence of sharp peaks (i.e., those whose width at half-height is in the range of 0.3 to 0.5 degrees 2θ) in an XRPD pattern, while the XRPD pattern of an amorphous substance is characterized by the presence of broad scattering peaks (i.e., those whose width at half-height is in the range of at least 8 to 12 degrees 2θ).

In one aspect, the acid solution comprises any suitable acid (e.g., hydrochloric acid (HCl), nitric acid ($HNO_3$), or sulfuric acid ($H_2SO_4$)). In one aspect, the acid is hydrochloric acid.

In another aspect, the base is any suitable base (e.g., sodium hydroxide (NaOH), potassium hydroxide (KOH), or ammonium hydroxide ($NH_4OH$)). In one aspect, the base is sodium hydroxide.

In yet another aspect, the pH is reduced to pH=1 or below. In a further aspect, when the pH is raised, it is increased to pH=10 or above.

In another aspect, onapristone is first dissolved in methanol, and the resulting solution allowed to dry yielding an onapristone/methanol solvate. If this resulting solvated form is heated at a temperature sufficient to desolvate the solid (e.g., around 100° C.) for the minimal amount of time (e.g., less than 10 minutes), amorphous onapristone is formed.

Yet another aspect provides compositions comprising onapristone (25%) in a polyvinylpyrrolidone VA64 copolymer matrix (i.e., onapristone/PVP VA 64).

Aspects provide methods of spray drying amorphous onapristone by spray drying onapristone/PVP VA 64 from a solution comprising about 8% w/w solids in methanol resulting in amorphous onapristone.

Another aspect provides compositions comprising onapristone and Kollidon® (polyvinylpyrrollidone) 30 (onapristone/Kollidon® 30). In another aspect, the composition comprises about 0.255 g of onapristone and about 0.777 g of Kollidon® 30.

Another aspect provides methods of making amorphous onapristone by heating onapristone/Kollidon® 30 until the Kollidon® 30 melts, forming a molten mixture wherein the onapristone is dissolved in the polymer melt. Next, the mixture is allowed to cool to room temperature and form a glassy solid of amorphous onapristone. In another aspect, the onapristone content of the glassy solid is about 24% w/w.

Another aspect provides compositions comprising onapristone and polyethylene glycol 8000 (Onapristone/Kollidon® 30). In another aspect, the composition comprises about 0.241 g of onapristone and about 0.700 g of polyethylene glycol 8000.

Further aspects provide methods of making amorphous onapristone by heating onapristone/polyethylene glycol 8000 until the polyethylene glycol 8000 melts forming a polymer melt, and the onapristone dissolves in the polymer melt forming a mixture. Next, the mixture is allowed to cool to room temperature and form a glassy solid of amorphous onapristone. In another aspect, the onapristone content of the glassy solid is about 25% w/w.

Another aspect provides compositions comprising onapristone and polyethylene glycol 3350 (onapristone/polyethylene glycol 3350). In another aspect, the composition comprises about 0.238 g of onapristone and about 0.762 g of polyethylene glycol 3350.

Further aspects provide methods of making amorphous onapristone by heating onapristone/polyethylene glycol 3350 until the polyethylene glycol 3350 melts forming a polymer melt, and the onapristone dissolves in the polymer melt forming a mixture. Next, the mixture is allowed to cool to room temperature and form a glassy solid of amorphous onapristone. In another aspect, the onapristone content of the glassy solid is about 23% w/w.

Another aspect provides compositions comprising onapristone and pyrrolidone K29/32 (onapristone/pyrrolidone K29/32). In another aspect, the composition comprises about 0.249 g of onapristone and about 0.784 g of pyrrolidone K29/32.

Further aspects provide methods of making amorphous onapristone by heating onapristone/pyrrolidone K29/32 until the pyrrolidone K29/32 melts forming a polymer melt, and the onapristone dissolves in the polymer melt forming a mixture. Next, the mixture is allowed to cool to room temperature and form a glassy solid of amorphous onapristone. In another aspect, the onapristone content of the glassy solid is about 24% w/w.

Another aspect provides compositions comprising onapristone, polyvinyl pyrrolidone K29/32, and polyethylene glycol 3350 (onapristone/pyrrolidone K29/32/PEG). In another aspect, the composition comprises about 0.258 g of onapristone, about 0.202 g of polyvinyl pyrrolidone K29/32, and about 0.503 g of polyethylene glycol 3350. In yet another aspect, the composition comprises about 0.242 g of onapristone, about 0.373 g of polyvinyl pyrrolidone K29/32, and about 0.384 g of polyethylene glycol 3350. In yet another aspect, the composition comprises about 0.241 g of onapristone, about 0.547 g of polyvinyl pyrrolidone K29/32, and about 0.197 g of polyethylene glycol 3350.

Further aspects provide methods of making amorphous onapristone by heating onapristone/pyrrolidone K29/32 until the polyvinyl pyrrolidone K29/32 and polyethylene glycol 3350 melts forming a polymer melt, and the onapristone dissolves in the polymer melt forming a mixture. Next, the mixture is allowed to cool to room temperature and form a glassy solid of amorphous onapristone.

Figure 1:
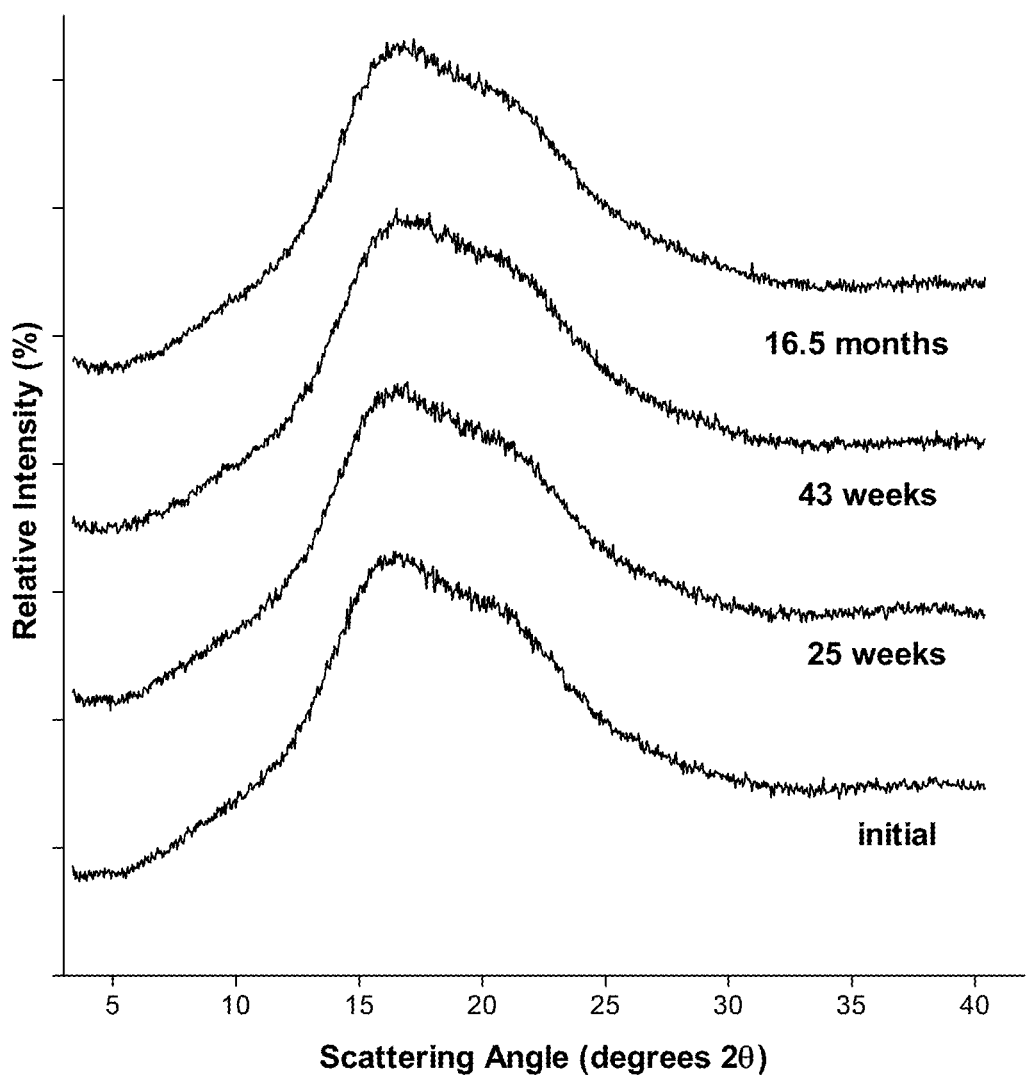
FIG. 1 shows exemplary X-ray powder diffraction patterns of onapristone produced by the pH-cycle method.

FIG. 1 shows X-ray powder diffraction patterns of onapristone as initially produced by the pH-cycle method, and stored under ambient conditions for 25 weeks, 43 weeks, and 16.5 months.

Figure 2:
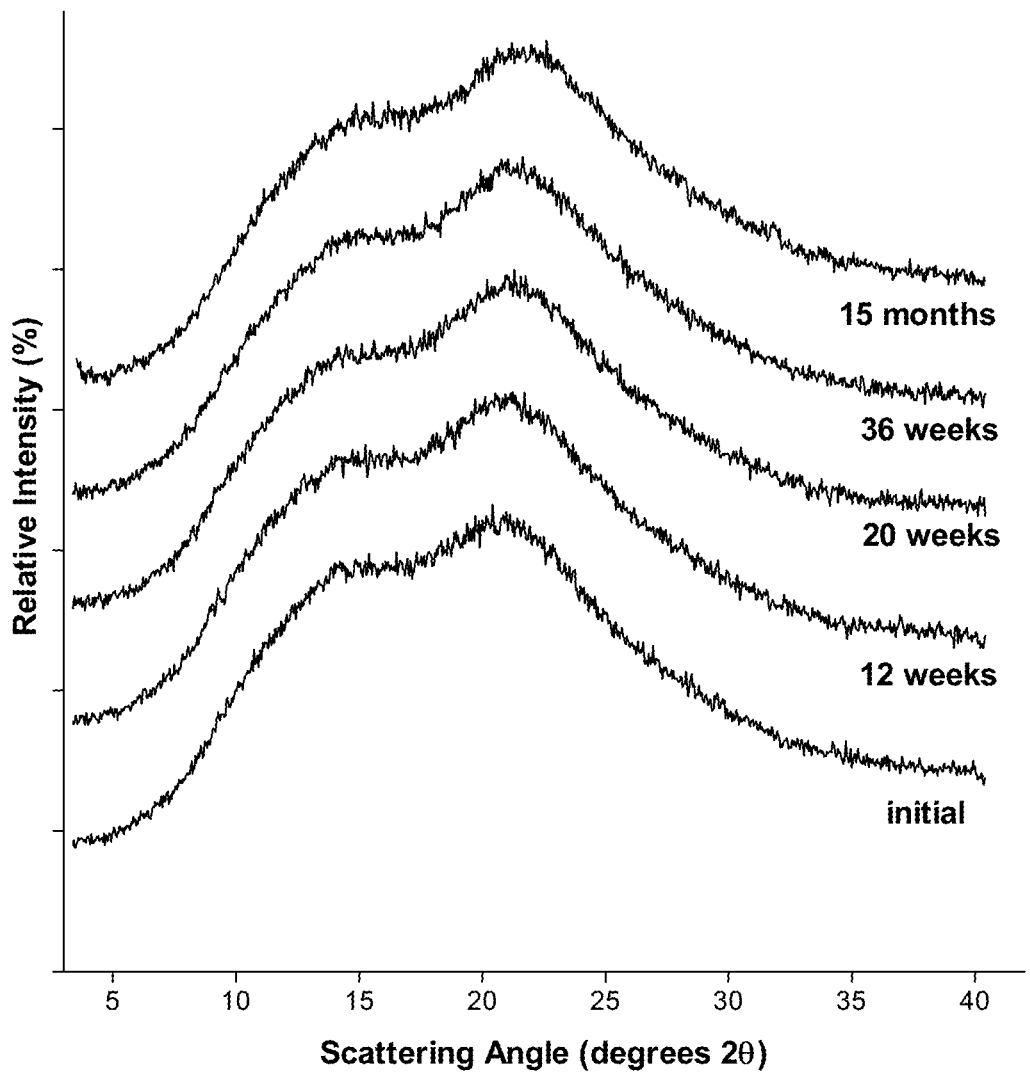
FIG. 2 shows exemplary X-ray powder diffraction patterns of 25% w/w onapristone dispersions (containing polyvinyl pyrrolidone VA64) produced by the spray-drying method, and stored for various time periods.

FIG. 2 shows X-ray powder diffraction patterns of 25% w/w onapristone dispersions (containing polyvinyl pyrrolidone VA64) produced by the spray-drying method, and stored under ambient conditions for 12 weeks, 20 weeks, 36 weeks, and 15 months.

Figure 3:
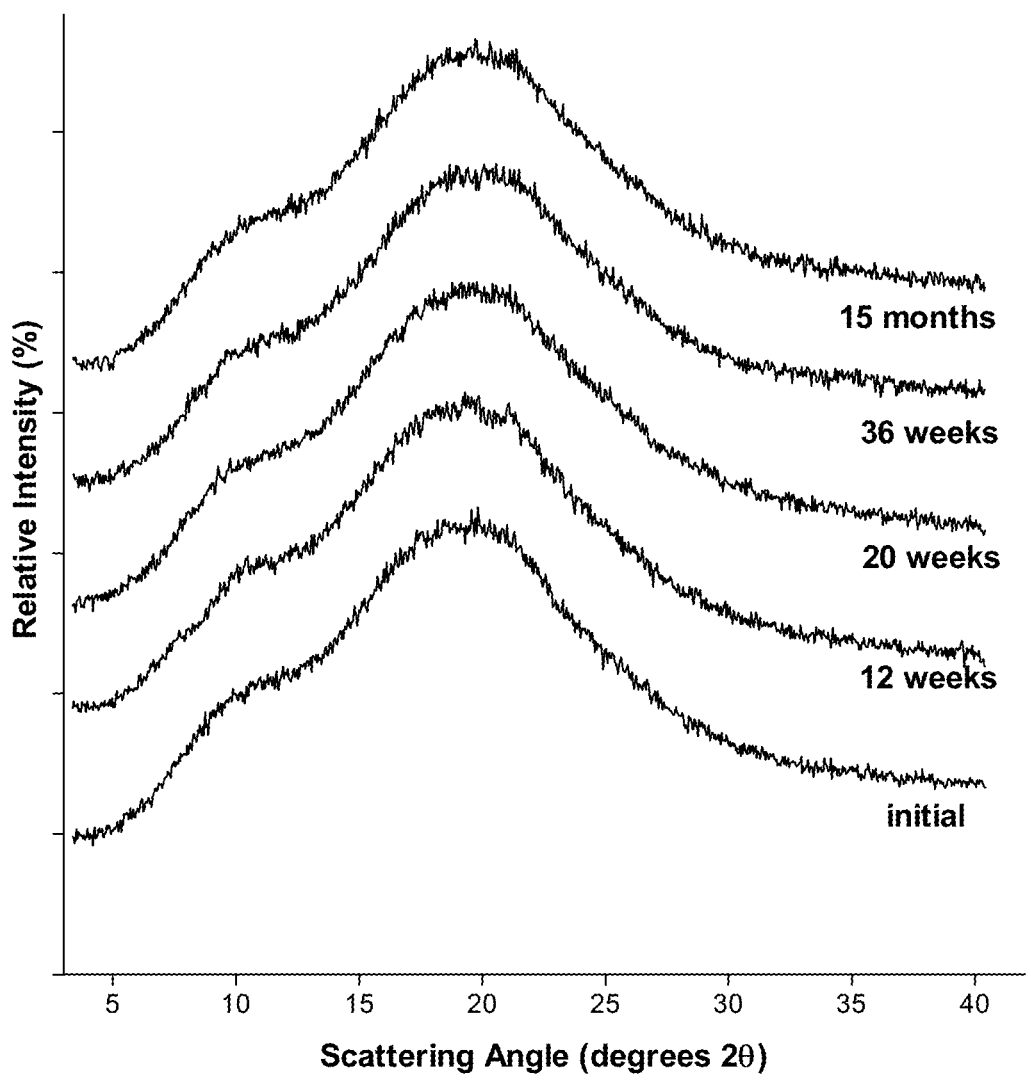
FIG. 3 shows exemplary X-ray powder diffraction patterns of 25% w/w onapristone dispersions (containing hydroxypropyl methylcellulose succinate M) produced by the spray-drying method, and stored for various time periods.

FIG. 3 shows X-ray powder diffraction patterns of 25% w/w onapristone dispersions (containing hydroxypropyl methylcellulose succinate M) produced by the spray-drying method, and stored under ambient conditions for 12 weeks, 20 weeks, 36 weeks, and 15 months.

Figure 4:
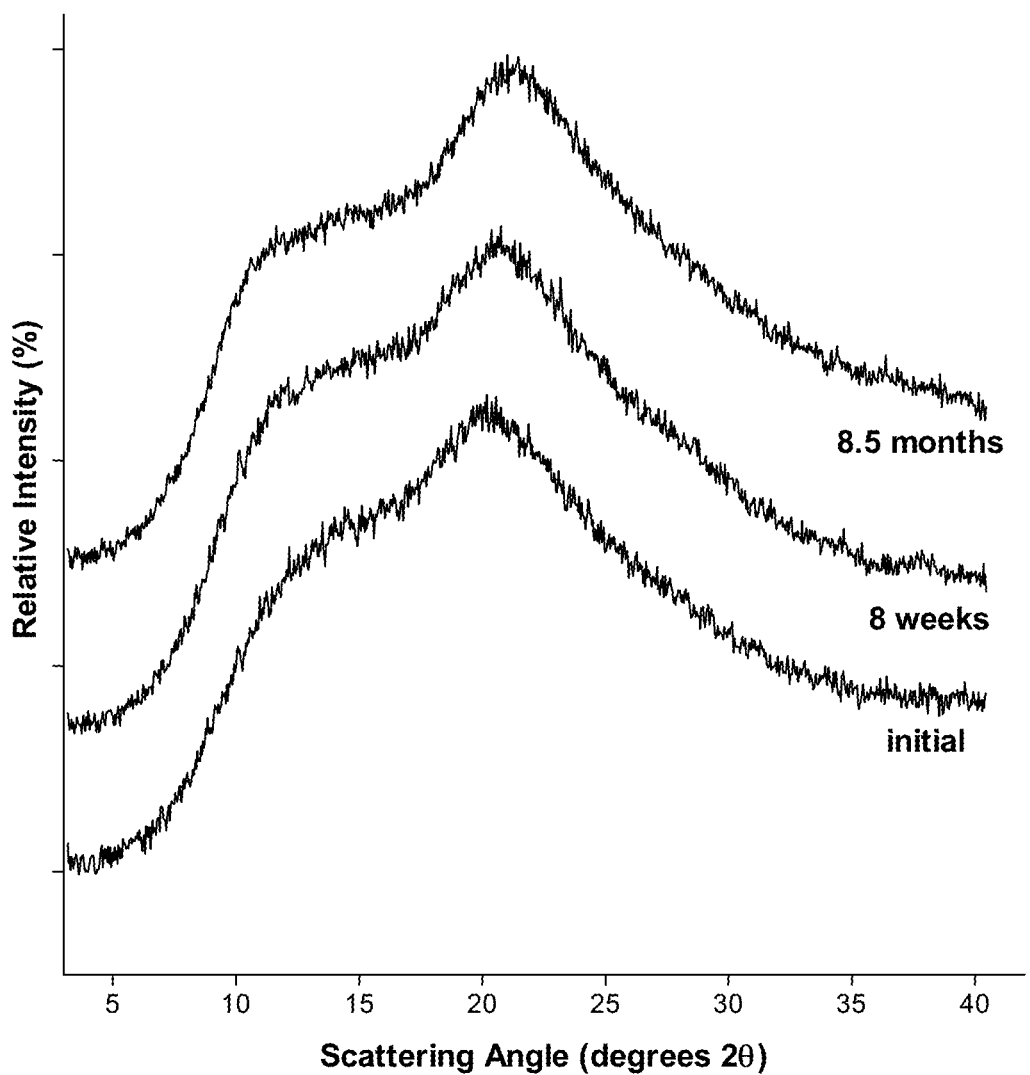
FIG. 4 shows exemplary X-ray powder diffraction patterns of approximately 25% w/w onapristone dispersions (containing Kollidon®® 30 (polyvinylpyrrolidone)) produced by the hot-melt method, and stored for various time periods.

FIG. 4 shows X-ray powder diffraction patterns of nominal 25% w/w onapristone dispersions (containing Kollidon® 30) produced by the hot-melt method, and stored under ambient conditions for 8 weeks and 8.5 months.

Figure 5:
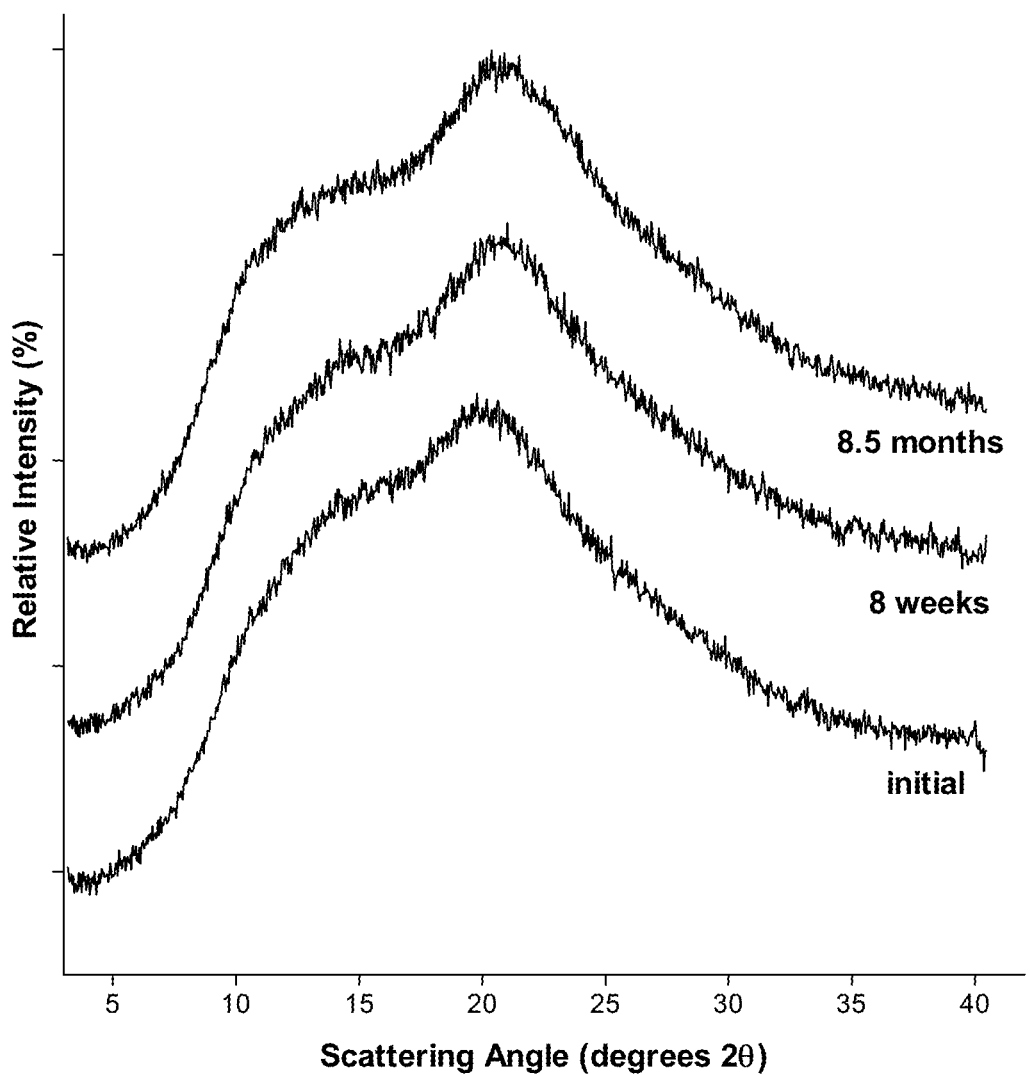
FIG. 5 shows exemplary X-ray powder diffraction patterns of approximately 25% w/w onapristone dispersions (containing polyvinyl pyrrolidone K29/32) produced by the hot-melt method, and stored for various time periods.

FIG. 5 shows X-ray powder diffraction patterns of nominal 25% w/w onapristone dispersions (containing polyvinyl pyrrolidone K29/32) produced by the hot-melt method, and stored under ambient conditions for 8 weeks and 8.5 months.

Figure 6:
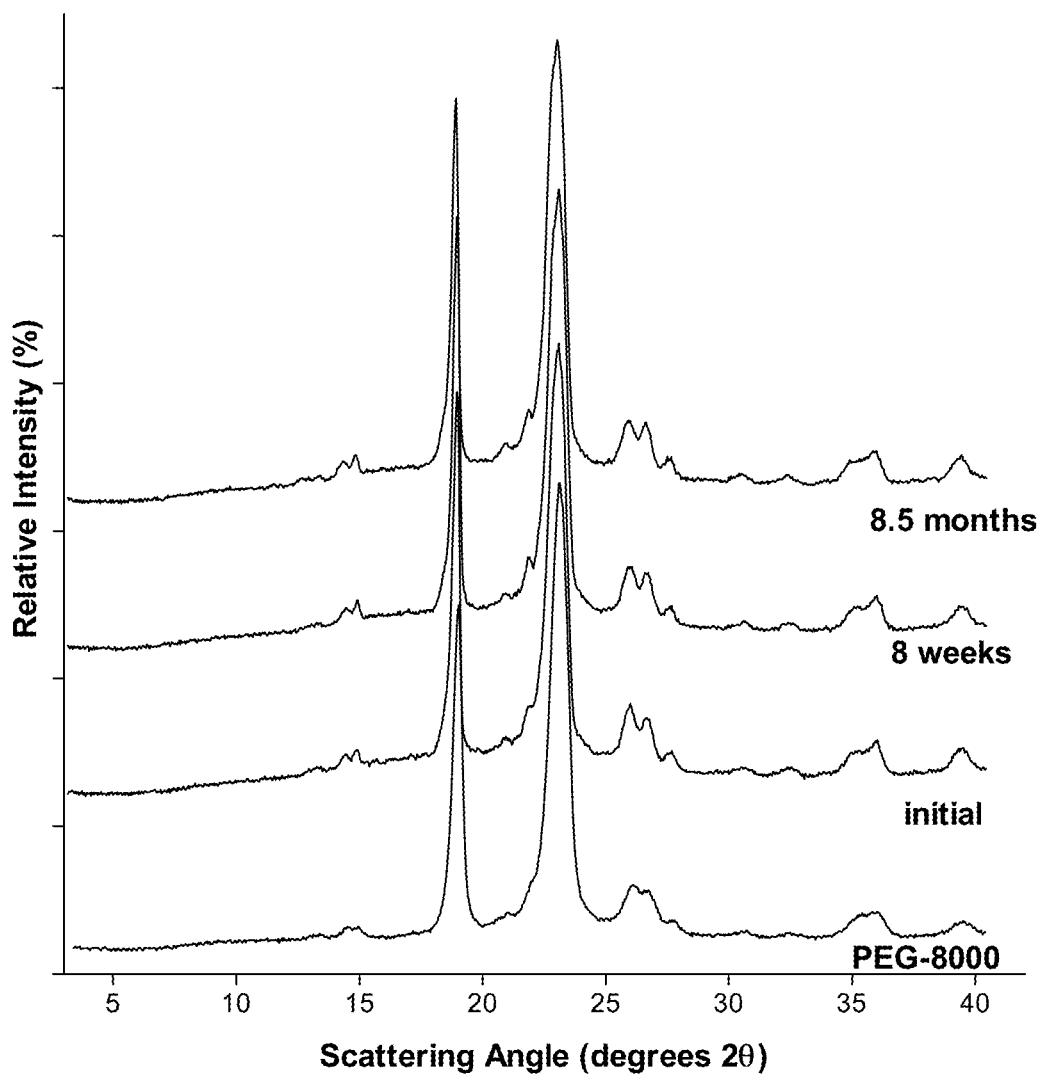
FIG. 6 shows exemplary X-ray powder diffraction patterns of approximately 25% w/w onapristone dispersions (containing polyethylene glycol 8000) produced by the hot-melt method, and stored for various time periods.

FIG. 6 shows X-ray powder diffraction patterns of nominal 25% w/w onapristone dispersions (containing polyethylene glycol 8000) produced by the hot-melt method, and stored under ambient conditions for 8 weeks and 8.5 months. The XRPD pattern for polyethylene glycol 8000 itself is shown for comparison purposes, demonstrating that all scattering peaks in the XRPD of the formulations were due entirely to the excipient.

Figure 7:
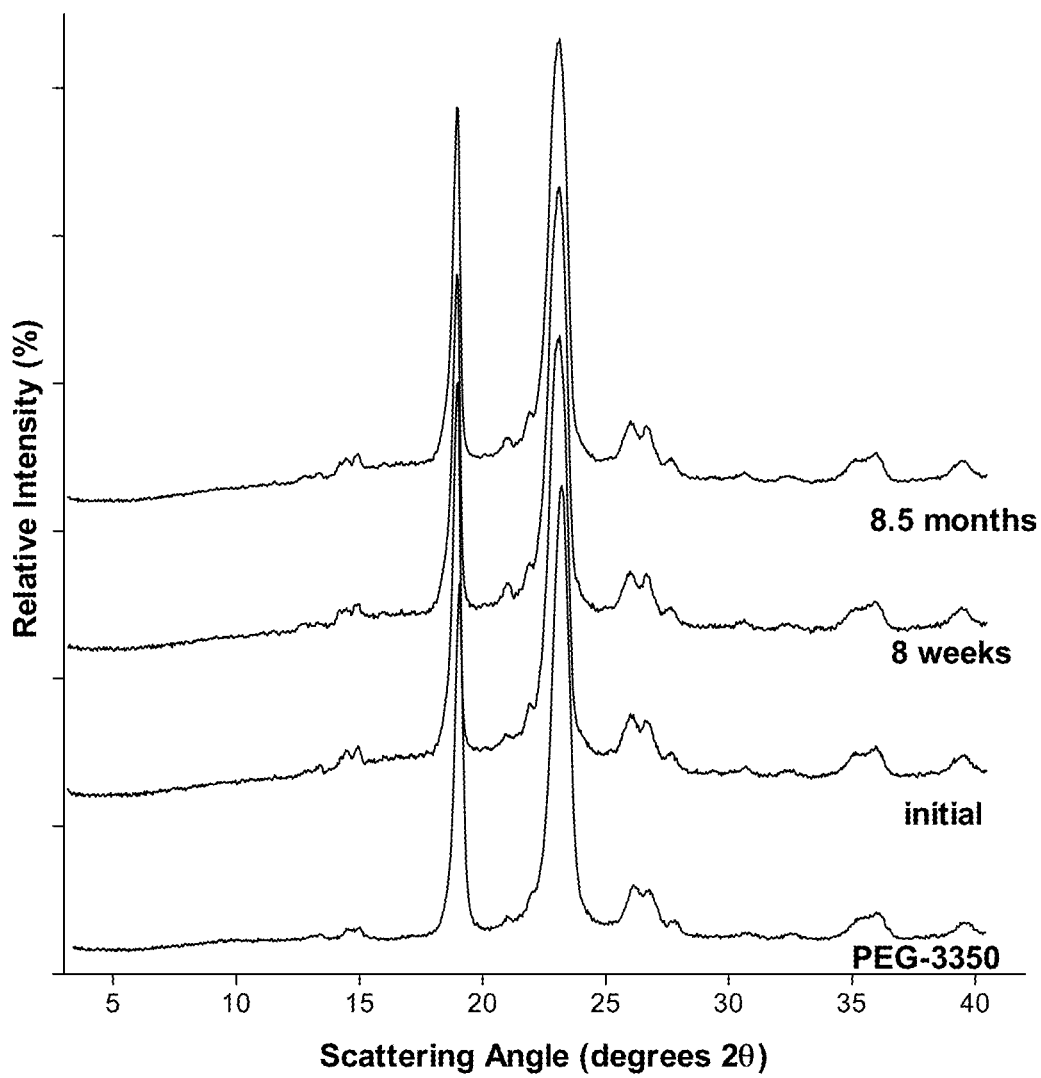
FIG. 7 shows exemplary X-ray powder diffraction patterns of approximately 25% w/w onapristone dispersions (containing polyethylene glycol 3350) produced by the hot-melt method, and stored for various time periods.

FIG. 7 shows X-ray powder diffraction patterns of nominal 25% w/w onapristone dispersions (containing polyethylene glycol 3350) produced by the hot-melt method, and stored under ambient conditions for 8 weeks and 8.5 months. The XRPD pattern for polyethylene glycol 3350 itself is shown for comparison purposes, demonstrating that all scattering peaks in the XRPD of the formulations were due entirely to the excipient.

FIG. 8 shows X-ray powder diffraction patterns of nominal 25% w/w onapristone dispersions (containing 27.1% w/w polyvinyl pyrrolidone K29/32 and 72.9% w/w polyethylene glycol 3350) produced by the hot-melt method, and stored under ambient conditions for 8 weeks and 8.5 months. The XRPD pattern for polyethylene glycol 3350 itself is shown for comparison purposes, demonstrating that all scattering peaks in the XRPD of the formulations were due entirely to the excipient.

FIG. 9 shows X-ray powder diffraction patterns of nominal 25% w/w onapristone dispersions (containing 49.3% w/w polyvinyl pyrrolidone K29/32 and 50.7% w/w polyethylene glycol 3350) produced by the hot-melt method, and stored under ambient conditions for 8 weeks and 8.5 months. The XRPD pattern for polyethylene glycol 3350 itself is shown for comparison purposes, demonstrating that all scattering peaks in the XRPD of the formulations were due entirely to the excipient.

FIG. 10 shows X-ray powder diffraction patterns of nominal 25% w/w onapristone dispersions (containing 73.5% w/w polyvinyl pyrrolidone K29/32 and 26.5% w/w polyethylene glycol 3350) produced by the hot-melt method, and stored under ambient conditions for 8 weeks and 8.5 months. The XRPD pattern for polyethylene glycol 3350 itself is shown for comparison purposes, demonstrating that all scattering peaks in the XRPD of the formulations were due entirely to the excipient.

FIG. 11 shows X-ray powder diffraction patterns of onapristone dispersions containing Kollidon® 30 produced by the solution-phase coprecipitate method. The nominal onapristone concentrations in the dispersions are indicated, and the XRPD pattern for Kollidon® 30 itself is shown for comparison purposes.

FIG. 12 shows X-ray powder diffraction patterns of onapristone dispersions containing polyvinylpyrrolidone K29/32 produced by the solution-phase coprecipitate method. The nominal onapristone concentrations in the dispersions are indicated, and the XRPD pattern for polyvinylpyrrolidone K29/32 itself is shown for comparison purposes.

FIG. 13 shows X-ray powder diffraction patterns of onapristone dispersions containing polyethylene glycol 3350 produced by the solution-phase coprecipitate method. The nominal onapristone concentrations in the dispersions are indicated, and the XRPD pattern for polyethylene glycol 3350 itself is shown for comparison purposes (demonstrating that all scattering peaks in the XRPD of the formulations were due entirely to the excipient).

FIG. 14 shows X-ray powder diffraction patterns of onapristone dispersions containing polyethylene glycol 8000 produced by the solution-phase coprecipitate method. The nominal onapristone concentrations in the dispersions are indicated, and the XRPD pattern for polyethylene glycol 8000 itself is shown for comparison purposes (demonstrating that all scattering peaks in the XRPD of the formulations were due entirely to the excipient).

FIG. 15 shows X-ray powder diffraction patterns of nominal 25% onapristone dispersions containing various amounts of Kollidon® 30 and polyethylene glycol 8000 produced by the solution-phase coprecipitate method. The relative percentages of the two polymers are indicated.

The onapristone amorphous forms can be used to treat a patient in need of treatment as described herein. The terms "treat," "prevent," or similar terms, as used herein, do not necessarily mean 100% or complete treatment or prevention. Rather, these terms refer to various degrees of treatment or prevention of a particular disease (e.g., 100%, 90%, 80%, 70%, 60%, 50%, 40%, 30%, 20%, 10%, 5%, or 1%) as recognized in the art as being beneficial. The terms "treatment" or "prevention" also refer to delaying onset of a disease for a period of time or delaying onset indefinitely. The term "treatment" or "treating" refers to administering a drug or treatment to a patient or prescribing a drug to a patient where the patient or a third party (e.g., caretaker, family member, or health care professional) administers the drug or treatment.

The onapristone amorphous forms also encompass derivatives. In one embodiment, the term "derivative" includes, but is not limited to, ether derivatives, acid derivatives, amide derivatives, ester derivatives and the like. Methods of preparing these derivatives are known to a person skilled in the art. For example, ether derivatives are prepared by the coupling of the corresponding alcohols. Amide and ester derivatives are prepared from the corresponding carboxylic acid by a reaction with amines and alcohols, respectively.

The onapristone amorphous forms also encompass hydrates or solvates of onapristone amorphous or crystalline forms (e.g., hemihydrate, monohydrate, dihydrate, trihydrate and the like). Hydrates or solvates of onapristone may be prepared by contacting onapristone with water or a solvent under suitable conditions to produce the hydrate or solvate of choice, for example, as described herein.

The onapristone amorphous forms also encompass metabolites of onapristone amorphous forms. "Metabolite" or "metabolites" refer to any substance produced from another substance by metabolism or a through a metabolic process of a living cell or organ.

Any of the amorphous onapristone forms described herein can be administered or used as starting materials to be administered orally, parenterally (IV, IM, depot-IM, SQ, and depot-SQ), sublingually, intranasally (inhalation), intrathecally, topically, or rectally. Dosage forms known to those of skill in the art are suitable for delivery of the onapristone amorphous forms described herein.

The onapristone amorphous compounds can be formulated into suitable pharmaceutical preparations such as tablets, capsules, or elixirs for oral administration or in sterile solutions or suspensions for parenteral administration. The onapristone amorphous compounds described herein can be formulated into pharmaceutical compositions using techniques and procedures well known in the art.

In one aspect, about 10 to about 200 mg of the onapristone amorphous compounds, or a physiologically acceptable salt, pro-drug, or co-crystal thereof can be compounded or used as a starting material for compounding with a physiologically acceptable vehicle, carrier, excipient, binder, preservative, stabilizer, flavor, etc., in a unit dosage form as called for by accepted pharmaceutical practice. The amount of active substance in compositions or preparations comprising the onapristone amorphous compounds is such that a suitable dosage in the range indicated is obtained.

In another aspect, the compositions can be formulated in a unit dosage form, each dosage containing from about 1 mg to about 1.2 g, or about 2.5 to about 200 mg of the active ingredient. The term "unit dosage from" refers to physically discrete units suitable as unitary dosages for human subjects and other mammals, each unit containing a predetermined quantity of active material calculated to produce the desired therapeutic effect, in association with one or more suitable pharmaceutical excipients.

In one aspect, one or more of the onapristone amorphous compounds are mixed with or used as starting materials mixed with a suitable pharmaceutically acceptable carrier to form compositions. Upon mixing or addition of the compound(s), the resulting mixture may be a solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. In one aspect, the effective concentration is sufficient for lessening or ameliorating at least one symptom of the disease, disorder, or condition treated and may be empirically determined.

Pharmaceutical carriers or vehicles suitable for administration of the onapristone amorphous compounds described herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

In another aspect, if the onapristone amorphous compounds exhibit insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

In another aspect, the onapristone amorphous compounds described herein may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

In another aspect, the onapristone amorphous compounds and compositions described herein can be enclosed in multiple or single dose containers. The enclosed compounds and compositions can be provided in kits, for example, including component parts that can be assembled for use. For example, an onapristone amorphous compound can be used as a starting material for a lyophilized form and a suitable diluent may be provided as a separated component for combination prior to use. A kit may include onapristone amorphous compound and a second therapeutic agent for co-administration. The onapristone amorphous compound and second therapeutic agent may be provided as separate component parts. A kit may include a plurality of containers, each container holding one or more unit dose of the onapristone amorphous compounds described herein. In one aspect, the containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of the onapristone amorphous compound in the pharmaceutical composition will depend on dissolution, absorption, metabolism, and excretion rates of the active compound, the dosage schedule, and amount administered as well as other factors known to those of skill in the art.

In another aspect, the active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action. The onapristone amorphous compounds can be used, for example, in combination with an antitumor agent, a hormone, a steroid, or a retinoid. The antitumor agent may be one of numerous chemotherapy agents (e.g., everolimus, trastuzumab, TM1-D, anti-HER2 drugs, bevacizumab, paclitaxel, docetaxel, taxanes, doxorubicin, liposomal doxorubicin, pegylated liposomal doxorubicin, anthracyclines, anthracenediones, carboplatin, cisplatin, 5-FU, gemcitabine and cyclophosphamide).

In one aspect, solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfate; chelating agents such as ethylenediaminetetraacetic acid (EDTA) or its disodium salt; buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropylene glycol, and mixtures thereof. Liposomal suspensions including tissue-targeted liposomes may also be suitable as pharmaceutically acceptable carriers. These may be prepared according to methods known in the art.

In another aspect, the onapristone amorphous compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, hydroxyl propyl methyl cellulose (HPMC), other cellulose derivatives, and the like. Methods for preparation of such formulations are known to those skilled in the art.

In yet another aspect, compounds employed in the methods of the disclosure may be administered enterally or parenterally. When administered orally, compounds employed in the methods of the disclosure can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods described herein need to be administered only once or twice daily.

The oral dosage forms can be administered to the patient 1, 2, 3, or 4 times daily. The onapristone amorphous compounds described herein can be administered either three or fewer times, or even once or twice daily. Hence, the onapristone employed in the methods of the disclosure be administered in oral dosage form. Whatever oral dosage form is used, they can be designed so as to protect the compounds employed in the methods described herein from the acidic environment of the stomach. Enteric coated tablets are well known to those skilled in the art. In addition, capsules filled with small spheres each coated to protect from the acidic stomach, are also well known to those skilled in the art.

The terms "therapeutically effective amount" and "therapeutically effective period of time" are used to denote treatments at dosages and for periods of time effective to reduce neoplastic cell growth. As noted above, such administration can be parenteral, oral, sublingual, transdermal, topical, intranasal, or intrarectal. In one aspect, when administered systemically, the therapeutic composition can be administered at a sufficient dosage to attain a blood level of the compounds of from about 0.01 µM to about 20 µM. For localized administration, much lower concentrations than this can be effective, and much higher concentrations may be tolerated. One of skill in the art will appreciate that such therapeutic effect resulting in a lower effective concentration of the ONA amorphous compound may vary considerably depending on the tissue, organ, or the particular animal or patient to be treated. It is also understood that while a patient may be started at one dose, that dose may be varied overtime as the patient's condition changes. In one aspect, the onapristone amorphous compounds can be used to inhibit the growth of tumors derived from tissue including, but not limited to, breast, brain, meningiomas, prostate, ovarian, endometrial, uterine leiomyoma, lung, and uterine tissues.

It should be apparent to one skilled in the art that the exact dosage and frequency of administration will depend on the particular compounds employed in the methods of the disclosure administered, the particular condition being treated, the severity of the condition being treated, the age, weight, general physical condition of the particular patient, and other medication the individual may be taking as is well known to administering physicians who are skilled in this art.

EXAMPLES

Example 1

Physical Form of Onapristone Compound

The physical form of onapristone, either as the bulk drug substance or in its compositions, was established using X-ray powder diffraction (XRPD). XRPD patterns were obtained using a Rigaku MiniFlex powder diffraction system, equipped with a horizontal goniometer operating in the θ/2θ mode. The X-ray source was nickel-filtered Kα emission of copper (1.54184 Å). Samples were packed into the sample holder using a back-fill procedure, and were scanned over the range of 3.5 to 40 degrees 2θ at a scan rate of 0.5 degrees 2θ/min. Using a data acquisition rate of 1 point per second, these scanning parameters equate to a step size of 0.0084 degrees 2θ. Calibration of the diffractometer system was effected using purified talc as a reference material. The intensity scale for all diffraction patterns was normalized so that the relative intensity of the most intense peak in the pattern equaled 100%.

Example 2

The pH-Cycle Method to Obtain Amorphous Onapristone

The onapristone molecule contains a functional group that is effectively a substituted aniline:

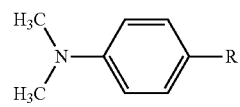

In one aspect, one would expect this group to be somewhat acidic. Using the pKa-Predictor module of the Physical Chemistry Program Suite (Advanced Chemical Laboratories, Toronto, Calif.), the pKa of this group was predicted to be 5.30±0.25. Using the predictive solubility module of the ACD program, it was determined that the protonated form of the compound is expected to be fairly soluble in water, while the neutral form is expected to be relatively insoluble in water.

In one aspect, 0.408 g of onapristone (0.91 mmol) was slurried in 25 mL of water, and then 0.5 mL of 2N HCl (1.0 mmol) was added. The solid completely dissolved in approximately 5 minutes, whereupon 2.0 mL of 0.5 N NaOH (1.0 mmol) was added. The precipitated onapristone was suction-filtered, and allowed to air-dry overnight.

The XRPD pattern of this product was obtained, and the lack of sharp scattering peaks demonstrated its amorphous character. After the initial characterization, the substance was placed in a glass vial, and stored under ambient conditions (temperature of 22-24° C.). The product was subsequently obtained after storage under ambient conditions for 25 weeks, 43 weeks, and 16.5 months. As shown in FIG. 1, the pH-cycled onapristone remained amorphous over the entire 16.5 month storage period.

Example 3

Spray-Drying Method to Obtain Amorphous Onapristone

Two samples of onapristone that had been spray-dried with excipients were prepared to have the following compositions:

Sample ID=SSF-PDS-027-001A comprising 25% onapristone in a matrix consisting of PVP VA64, and was spray-dried from a solution consisting of 8% w/w solids in methanol.

Sample ID=SSF-PDS-027-001B comprising 25% onapristone in a matrix consisting of HPMCAS-M, and was spray-dried from a solution consisting of 8% w/w solids in methanol.

XRPD patterns of these samples were obtained when initially received and after 12 weeks, 20 weeks, 36 weeks, and 15 months had elapsed. The XRPD patterns obtained for sample SSF-PDS-027-001A are collected in FIG. 2, while the XRPD patterns obtained for sample SSF-PDS-027-001B are collected in FIG. 3.

Examination of FIGS. 2 and 3 reveals that both spray-dried dispersions were amorphous when initially prepared, and that they both remained amorphous over the 315 month storage period.

Example 4

Hot-Melt Method to Obtain Amorphous Onapristone

Binary Formulations

Four formulations were prepared to determine if a hot-melt procedure was capable of producing dispersions containing amorphous onapristone. The experimental details associated with these formulations are as follows:

Preparation 1: 0.255 g of onapristone and 0.777 g of Kollidon® 30 were weighed directly into a 150 mL beaker, and then heated on a hot plate until the polymer had melted and the onapristone dissolved in the melt. After that, the beaker and contents were allowed to cool back to room temperature, whereupon the glassy solid was broken up and then ground into a powder. The onapristone content of this sample was 24.7% w/w.

Preparation 2: 0.241 g of onapristone and 0.700 g of polyethylene glycol 8000 were weighed directly into a 150 mL beaker, and then heated on a hot plate until the polymer had melted and the onapristone dissolved in the melt. After that, the beaker and contents were allowed to cool back to room temperature, whereupon the glassy solid was broken up and then ground into a powder. The onapristone content of this sample was 25.6% w/w.

Preparation 3: 0.238 g of onapristone and 0.762 g of polyethylene glycol 3350 were weighed directly into a 150 mL beaker, and then heated on a hot plate until the polymer had melted and the onapristone dissolved in the melt. After that, the beaker and contents were allowed to cool back to room temperature, whereupon the glassy solid was broken up and then ground into a powder. The onapristone content of this sample was 23.8% w/w.

Preparation 4: 0.249 g of onapristone and 0.784 g of polyvinyl pyrrolidone K29/32 were weighed directly into a 150 mL beaker, and then heated on a hot plate until the polymer had melted and the onapristone dissolved in the melt. After that, the beaker and contents were allowed to cool back to room temperature, whereupon the glassy solid was broken up and then ground into a powder. The onapristone content of this sample was 24.1% w/w.

The XRPD pattern of formulations containing polyvinyl pyrrolidone (i.e., preparations 1 and 4) are shown in FIGS. 4 and 5, respectively. Also shown in FIGS. 4 and 5 are the XRPD patterns of the same products after each had been stored under ambient conditions for time periods of 8 weeks and 8.5 months. Since no sharp peaks attributable to crystalline onapristone were detected in the XRPD of the preparations, it is concluded that the drug substance remained amorphous over the entire 8.5 month storage period.

The XRPD pattern of formulations containing polyethylene glycol (i.e., preparations 2 and 3) are shown in FIGS. 6 and 7. Also shown in FIGS. 6 and 7 are the XRPD patterns of the same products after each had been stored under ambient conditions for time periods of 8-weeks and 8.5 months, as well as the XRPD patterns of the polyethylene glycol polymers used to form the products.

In addition to a number of weak scattering features, the XRPD patterns of the PEG polymer products are dominated by two scattering peaks at approximately 19 and 23 degrees 2θ. All of the polymer peaks were observed in the XRPD patterns of the dispersions, but no additional peaks attributable to crystalline onapristone were detected in the XRPD patterns of the preparations. Therefore, the drug substance remained amorphous over the entire 8.5 month storage period.

Ternary Formulations

Three additional formulations were prepared to determine if the inclusion of varying amounts of polyethylene glycol could produce less brittle dispersions for products prepared using the hot-melt procedure. The experimental details associated with these formulations are as follows:

Preparation 5: 0.258 g of onapristone, 0.202 g of polyvinyl pyrrolidone K29/32, and 0.543 g of polyethylene glycol 3350 were weighed directly into a 150 mL beaker, and then heated on a hot plate until the polymers had melted and the onapristone dissolved in the melt. After that, the beaker and contents were allowed to cool back to room temperature, whereupon the glassy solid was broken up and then ground into a powder. The onapristone content of this sample was 25.7% w/w, and the PVP content in this sample was 27.1% w/w (relative to the total polymer concentration).

Preparation 6: 0.242 g of onapristone, 0.373 g of polyvinyl pyrrolidone K29/32, and 0.384 g of polyethylene glycol 3350 were weighed directly into a 150 mL beaker, and then heated on a hot plate until the polymers had melted and the onapristone dissolved in the melt. After that, the beaker and contents were allowed to cool back to room temperature, whereupon the glassy solid was broken up and then ground into a powder. The onapristone content of this sample was 24.2% w/w, and the PVP content in this sample was 49.3% w/w (relative to the total polymer concentration).

Preparation 7: 0.241 g of onapristone, 0.547 g of polyvinyl pyrrolidone K29/32, and 0.197 g of polyethylene glycol 3350 were weighed directly into a 150 mL beaker, and then heated on a hot plate until the polymers had melted and the onapristone dissolved in the melt. After that, the beaker and contents were allowed to cool back to room temperature, whereupon the glassy solid was broken up and then ground into a powder. The onapristone content of this sample was 24.5% w/w, and the PVP content in this sample was 73.5% w/w (relative to the total polymer concentration).

The XRPD patterns of these latter three preparations are shown in FIGS. 8-10, respectively, along with the XRPD patterns of the polyethylene glycol 3350 excipient. Also shown in FIGS. 8-10 are the XRPD patterns of the same products after each had been stored under ambient conditions for time periods of 8 weeks and 8.5 months. The XRPD patterns of the hot-melt dispersions were dominated by the two scattering peaks (at approximately 19 and 23 degrees 28) associated with the PEG-3350, but no additional peaks attributable to crystalline onapristone were detected in the XRPD of the preparations. Therefore, the drug substance remained amorphous over the 8 week storage period. In addition, all three dispersions were easily dislodged from the beaker, and their rendition into powder was straight-forward.

Example 5

Solution-Phase Method to Obtain Amorphous Onapristone

Binary Formulations

Four formulation systems were prepared to determine if a solution-phase procedure was capable of producing dispersions containing amorphous onapristone. Each system was based on the use of a specific polymer, but containing different amounts of onapristone. The experimental details associated with these formulations are as follows.

For preparations within the Kollidon® 30 system, the requisite amount of onapristone and Kollidon® 30 were weighed directly into a 150 mL beaker, and 30 mL of absolute isopropanol was added to the beaker. The contents were stirred until dissolution was complete, whereupon the solution was poured into an evaporating dish and allowed to completely air-dry. The Kollidon® 30 preparations had the following compositions:

| Nominal Polymer Percentage | Mass Onapristone Taken (g) | Mass Kollidon® 30 Taken (g) | Actual Polymer Percentage |
|---|---|---|---|
| 6 | 0.0314 | 0.4734 | 6.22 |
| 12 | 0.0594 | 0.4466 | 11.74 |
| 18 | 0.0918 | 0.4178 | 18.01 |
| 24 | 0.1252 | 0.3812 | 24.72 |

The XRPD patterns obtained for the Kollidon® 30 formulation series are shown in FIG. 11. Since no sharp peaks attributable to crystalline onapristone were detected in the XRPD of the preparations, it was concluded that the drug substance was amorphous in the products.

For preparations within the polyvinylpyrrolidone K29/32 system, the requisite amount of onapristone and Kollidon® 30 were weighed directly into a 150 mL beaker, and 30 mL of absolute isopropanol was added to the beaker. The contents stirred until dissolution was complete, whereupon the solution was poured into an evaporating dish and allowed to completely air-dry. The polyvinylpyrrolidone K29/32 preparations had the following compositions:

| Nominal Polymer Percentage | Mass Onapristone Taken (g) | Mass PVP K29/32 Taken (g) | Actual Polymer Percentage |
|---|---|---|---|
| 6 | 0.0313 | 0.4717 | 6.22 |
| 12 | 0.0604 | 0.4399 | 12.07 |
| 18 | 0.0903 | 0.4087 | 18.10 |
| 24 | 0.1212 | 0.3881 | 23.80 |

The XRPD patterns obtained for the polyvinylpyrrolidone K29/32 formulation series are shown in FIG. 12. Since no sharp peaks attributable to crystalline onapristone were detected in the XRPD of the preparations, it was concluded that the drug substance was amorphous in the products.

For preparations within the polyethylene glycol 3350 system, the requisite amount of onapristone and polyethylene glycol 3350 were weighed directly into a 150 mL beaker, and 30 mL of absolute isopropanol was added to the beaker. The contents were heated and stirred until dissolution was complete, whereupon the solution was poured into an evaporating dish and allowed to completely air-dry. The polyethylene glycol 3350 preparations had the following compositions:

| Nominal Polymer Percentage | Mass Onapristone Taken (g) | Mass PEG 3350 Taken (g) | Actual Polymer Percentage |
|---|---|---|---|
| 6 | 0.0311 | 0.4651 | 6.27 |
| 12 | 0.0598 | 0.4400 | 11.96 |
| 18 | 0.0907 | 0.4127 | 18.02 |
| 24 | 0.1183 | 0.3846 | 23.52 |

The XRPD patterns obtained for the polyethylene glycol 3350 formulation series are shown in FIG. 13. All of the observed scattering peaks were associated with the polyethylene glycol 3350, and no sharp peaks attributable to crystalline onapristone were detected in the XRPD of the preparations. The drug substance was amorphous in the products.

For preparations within the polyethylene glycol 8000 system, the requisite amount of onapristone and polyethylene glycol 8000 were weighed directly into a 150 mL beaker, and 30 mL of absolute isopropanol was added to the beaker. The contents were heated and stirred until dissolution was complete, whereupon the solution was poured into an evaporating dish and allowed to completely air-dry. The polyethylene glycol 8000 preparations had the following compositions:

| Nominal Polymer Percentage | Mass Onapristone Taken (g) | Mass PEG 8000 Taken (g) | Actual Polymer Percentage |
|---|---|---|---|
| 6 | 0.0318 | 0.4829 | 6.18 |
| 12 | 0.0628 | 0.4329 | 12.67 |
| 18 | 0.0900 | 0.4107 | 17.97 |
| 24 | 0.1174 | 0.3778 | 23.71 |

The XRPD patterns obtained for the polyethylene glycol 8000 formulation series are shown in FIG. 14. All of the observed scattering peaks were associated with the polyethylene glycol 8000, and no sharp peaks attributable to crystalline onapristone were detected in the XRPD of the preparations. The drug substance was amorphous in the products.

Ternary Formulations

Since coprecipitate formulations with superior handling characteristics can often be prepared through the use of more than one polymer, the Kollidon® 30/polyethylene glycol 8000 system was studied to determine if a solution-phase procedure was capable of producing dispersions containing amorphous onapristone. The systems contained a nominal 25% amount of onapristone, and had the following compositions:

| Nominal PVP/ PEG Percentage | Mass Onapristone Taken (g) | Actual Onapristone Percentage | Mass Kollidon ® 30 Taken (g) | Mass PEG 8000 Taken (g) | Actual Polymer Percentages |
|---|---|---|---|---|---|
| 26% PVP/ 74% PEG | 0.128 | 24.52 | 0.103 | 0.291 | PVP = 26.14% PEG = 73.86% |
| 50% PVP/ 50% PEG | 0.123 | 23.61 | 0.198 | 0.200 | PVP = 49.75% PEG = 50.25% |
| 74% PVP/ 26% PEG | 0.123 | 22.61 | 0.312 | 0.109 | PVP = 74.11% PEG = 25.89% |

The XRPD patterns obtained for the solution-phase ternary coprecipitate formulations are shown in FIG. 15. All of the observed scattering peaks were associated with the polyethylene glycol 8000, and no sharp peaks attributable to crystalline onapristone were detected in the XRPD of the preparations. The drug substance was amorphous in the ternary products.

Although the above description refers to particular aspects, it is to be understood that these aspects are merely illustrative. It will be apparent to those skilled in the art that various modifications and variations can be made to the amorphous forms and methods described herein. Thus, it is intended that the present description include modifications and variations that are within the scope of the appended claims and their equivalents.

What is claimed is:

1. A method of making a stable amorphous onapristone precipitate comprising:
   mixing onapristone and water to form an onapristone slurry;
   mixing at least one equivalent of an acid solution with the onapristone slurry to form a onapristone solution, wherein the pH of the onapristone solution mixed with the acid is about 1 or below;
   mixing at least one equivalent of a base to the onapristone solution to form the stable amorphous onapristone precipitate, wherein the pH of the onapristone solution mixed with the base is about 10 or above;
   isolating the stable amorphous onapristone precipitate by filtration; and
   drying the stable amorphous onapristone precipitate, wherein the dried stable amorphous onapristone precipitate remains amorphous for at least 25 weeks.

2. The method of claim 1, wherein the acid solution comprises an acid selected from the group consisting of hydrochloric acid, nitric acid, and sulfuric acid.

3. The method of claim 1, wherein the base is selected from the group consisting of sodium hydroxide, potassium hydroxide, and ammonium hydroxide.

4. The method of claim 1, wherein the amorphous onapristone precipitate remains amorphous for at least 16.5 months.

5. The method of claim 1, wherein the amorphous onapristone precipitate does not contain crystalline onapristone.

6. The method of claim 1, wherein the XPRD pattern of the amorphous onapristone precipitate does not contain any sharp peaks.

7. The method of claim 1, further comprising storing the dried stable amorphous under ambient conditions for at least 25 weeks, wherein the onapristone precipitate remains amorphous for the at least 25 weeks.

* * * * *